United States Patent [19]
Sampath et al.

[11] Patent Number: 5,928,940
[45] Date of Patent: Jul. 27, 1999

[54] MORPHOGEN-RESPONSIVE SIGNAL TRANSDUCER AND METHODS OF USE THEREOF

[75] Inventors: Kuber T. Sampath, Holliston, Mass.; Kohsuke Takeda, Ichikawa; Hidenori Ichijo, Tokyo, both of Japan

[73] Assignee: Creative BioMolecules, Inc., Boston, Mass.

[21] Appl. No.: 08/727,118

[22] Filed: Oct. 8, 1996

Related U.S. Application Data

[60] Provisional application No. 60/025,311, Sep. 24, 1996.
[51] Int. Cl.$^6$ .............................. C12N 5/00; C12N 15/00; C07H 21/04
[52] U.S. Cl. ................................ 435/325; 435/6; 435/7.1; 435/320.1; 536/23.5; 536/24.31; 935/9; 935/66
[58] Field of Search .................................. 536/23.1, 23.5, 536/24.1, 24.5; 435/6, 7.1, 320.1, 325; 935/9, 66

[56] References Cited

U.S. PATENT DOCUMENTS

| | | | |
|---|---|---|---|
| 5,106,626 | 4/1992 | Parsons et al. | 424/423 |
| 5,578,708 | 11/1996 | Okazaki et al. | 530/399 |
| 5,585,479 | 12/1996 | Hoke et al. | 536/24.5 |

FOREIGN PATENT DOCUMENTS

| | | |
|---|---|---|
| 0148155 | 7/1985 | European Pat. Off. . |
| 0416578 | 3/1991 | European Pat. Off. . |
| WO90/03733 | 4/1990 | WIPO . |
| WO91/02744 | 3/1991 | WIPO . |
| WO 92/15323 | 9/1992 | WIPO . |
| WO93/05172 | 3/1993 | WIPO . |
| WO 94/03200 | 2/1994 | WIPO . |
| WO 94/06399 | 3/1994 | WIPO . |
| WO96/38590 | 12/1996 | WIPO . |

OTHER PUBLICATIONS

Wang et al. (1988) "Purification and characterization of other distinct bone–inducing proteins," *Proc. Natl. Acad. Sci. USA*, 85:9484–9488.

Wozney et al. (1988) "Novel Regulators of Bone Formation: Molecular Clones and Activities," 242 *Science* 1528–1534.

Katagiri et al. (1990), "The non–osteogenic mouse pluripotent cell line, C3H10T1/2, is induced to differentiate into osteoblastic cells by recombinant human bone morphogenetic protein–2," 172 *Biochem. Biophys. Res. Commun.* 295–299.

Smith et al. (1990) "Identification of a Potent Xenopus Mesoderm Inducing Factor as a Homologue of Activin A," 345 *Nature* 729–731.

Takuwa et al. (1991)"Bone morphogenetic protein–2 stimulates alkaline phosphatase activity and collagen synthesis in cultured osteoblastic cells", 174 *Biochem Biophys. Res. Commun.* 96–101.

Knutsen et al. (1992) "Evidence That Osteogenic Protein–1 (OP–1) May Modulate Its Effects On Human Bone Cell Proliferation (HBC) By Regulating The Local Production of Insulin–Like Growth Factors," 7 *Bone & Min. Res.* S104–147.

Sampath et al. (1992) "Recombinant Human Osteogenic Protein–1 (hOP–1) Induced New Bone Formation in vivo with a Specific Activity Comparable with Natural Bovine Osteogenic Protein and Stimulated Osteoblast Proliferation and Differentiation in vitro," 267 *J. Biol. Chem.* 20352–20362.

Asahina, I. et al. (1993) "Human Osteogenic Protein–1 Induces both Chondroblastic and Osteoblastic Differentiation of Osteoprogenitor Cells Derived from Newborn Rat Calvaria", 123 *J. Cell Biol.* 921–933.

Knutsen et al. (1993) "Osteogenic Protein–1 Stimulates Proliferation and Differentiation of Human Bone Cells In Vitro" 194 *Biochem. Biophys. Res. Comm.* 1352–1358.

Ogata, T. et al. (1993) "Bone morphogenetic protein–2–transiently enhanced expression of a gene, Id (inhibitor of differentiation), enclodinga helix–loop–helix molecule in ostoblast–like cells," 90 *Proc. Natl. Acad. Sci. USA* 9219–9222.

Perides et al. (1993) "Osteogenic Protein–1 Regulated L1 and Neural Cell Adhesion Molecule Gene Expression in Neural Cells," 268 *J.Biol. Chem.* 25197–25205.

Suzuki, A. et al. (1993) "Differential Expression of Xenopus BMPs in early embryos and tissues" 10 *Zoolog Sic* (Japan) 175–178.

Graff, J.M. et al. (1994), "Studies with a Xenopus BMP receptor suggest that ventral mesodern–inducing signals override dorsal signals in vivo," 79 *Cell* 169–179.

Katagiri et al. (1994), "Bone Morphogenetic Protein–2 Converts the Differentiation Pathway of C2C12 Myoblasts into the Osteoblast Lineage," 127 *J. Cell Biol.* 1755–1766.

Knutsen et al. (1994) "Regulation of Insulin–Like Growth Factor (IGF) System Components by Osteogenic Protein–1 (OP–1) in Human Bone Cells," ¯Endocrinology, (In Press).

Liu et al. (1994) "Simultaneous Detection of Multiple Bone–Related mRNAs and Protein Expression During Osteoblast Differentiation: Polymerase Chain Reaction and Immunocytochemical Studies at the Single Cell Level," 166 *Dev. Biol.* 220–234.

(List continued on next page.)

*Primary Examiner*—Bruce R. Campell
*Attorney, Agent, or Firm*—Testa, Hurwitz & Thibeault, LLP

[57] ABSTRACT

A novel gene, DD-10, and its encoded polypeptide chain, DD-10, expressed during early onset of morphogen-induced mammalian tissue morphogenesis, now has been discovered. Accordingly, the invention identifies a new gene which is a novel biological marker of cell differentiation and tissue morphogenesis, particularly of chondroblast or osteoblast cell differentiation and bone tissue morphogenesis. Disclosed are: (a) methods and compositions for screening for and producing morphogen analogs; (b) novel morphogen analogs; (c) downstream inducers of morphogenesis; (d) a novel marker for evaluating morphogen or morphogen analog dosing; and (e) therapeutic methods and compositions using these analogs and/or downstream inducers.

29 Claims, 13 Drawing Sheets

OTHER PUBLICATIONS

Maliakal, J.C. et al. (1994) "Osteogenic Protein–1 (BMP–7) Inhibits Cell Proliferation and Stimulates the Expression of Markers Characteristic of Osteoblast Phenotype in Rate Osteosarcoma (17/2.8) cells," 11 *Growth Factors* (Swiss) 227–34.

Suzuki, A. et al. (1994), "A truncated bone morphogenetic protein receptor affects dorsal–ventral patterning in the early Xenopus embryo," 91 *Proc. Natl. Acad. Sci. USA* 10255–10259.

Chen, P. et al. (1995) "Osteogenic Protein–1 promotes growth and maturation of chick sternal chondrocytes in serum free cultures", 108 *J. Cell Science* 105–114.

Hentunen, T.A., et al. (1995) "Effects of Recombinant Human Osteogenic Protein–1 on the Differentiation of Osteoclast–like Cells and Bone Resorption", 209 *Biochem Biophys Res Commun* (US), 433–443.

Kitten, A.M. et al. (1995) "Osteogenic Protein–1 enhances phenotypic expression in ROS 17/2.8 cells," 269 *Am. J. Physiol.* E918–E926.

Knutsen, R. et al. (1995) "Regulation of Insulin–like Growth Factor System Components by Osteogenic Protein–1 in Human Bone Cells", 136 *Endocrinology* (US) 857–865.

Mahony et al. (1995), "A type 1 serine/threonine kinase receptor that can dorsalize mesoderm in Xenopus" 92 *Proc. Natl. Acad. Sci. USA* 6474–6478.

Schmidt et al. (1995), "Localized BMP–4 mediates dorsal/ventral patterning in the early Xenopus embryo," 169 *Devel. Biol.* 37–50.

Asahina, I. et al. (1996) "Human Osteogenic Protein–1 Induces Chondroblastic, Osteoblastic, and/or Adipocytic Differentiation of Clonal Murine Target Cells" 222 *Exp. Cell Res.* 38–47.

Cook, S.D. et al. (1996) "Osteogenic Protein–1," 324 *Clin. Orthop. and Rel. Res.* 29–38.

Martinovic, S. et al (1996) "Osteogenic Protein–1 is Produced by Human Fetal Trophoblasts In Vivo and Regulates the Synthesis of Chorionic Gonadotropin and Progesterone by Trophoblasts In Vitro," 34 *Eur. J. Clin. Chem. Clin. Biochem.* 103–109.

Massague, J. (1996) "TGFβ Signaling: Receptors, Transducers, and Mad Proteins," 85 *Cell* 947–950.

Solursh, M. et al. (1996) "Osteogenic Protein–1 is Required for Mammalian Eye Development," 218 *Biochem. Biophys. Res. Comm.* 2:438–443.

Takeda, K. et al. Japanese Meeting Abstract (Oct. 14, 1996) "cDNA cloning and functional analysis of an early–responsive gene induced by OP–1".

Yeh, L–C C. et al (1996) "Osteogenic Protein–1–Mediated Insulin–Like Growth Factor Gene Expression in Primary Cultures of Rat Osteoblastic Cells," 137 *Endocrinology* 1921–1931.

Ichijo, H. et al., (1996), "Signal Transduction of BMP". Abstract from the 5th International Bone Forum, "The Molecular and Cell Biology of Bone" Yokohama Prince Hotel, Nov. 14–15, 1996.

CF Bennett (1996) Science 271: 434.

JD Watson et al (1987) Molecular Biology of the Gene pp. 703–707.

JF Milligan et al (1993) J Med Chem 36: 1923–1937.

P Westermann et al (1989) Biomed Biochim Acta 48: 85–93.

N Miller et al (1994) Parasitology Today 10: 92–97.

RA Stull et al (1995) Pharmaceutical Research 12: 465–483.

S Wu–Pong (1994) Pharmaceutical Technology 118: 102–114.

RW Wagner (1994) Nature 372: 333–335.

Y Rojanasakul (1996) Advanced Drug Delivery Reviews 18: 115–131.

JC Szucsik et al (1995) Genomics 28: 154–162.

B Zhang et al (1992) Proc Natl Acad Sci USA 89: 7541–7545.

K Ray (1991) J Biol Chem 266: 6221–6229.

AFA Smit et al (Dec. 18, 1994) GenBank accession No. U17092. Accessed Dec. 18, 1997.

```
GAAGTGTGCTATTCTACCAGCTATTTGGTATCTCTAGGGCAACAAACTTGACAATCAAGATCAGCTACCACATGCCTCTC    80
TCCTCGATAAAGAGCAAGCTGCGAAGGGCGATTACAGCTGGACACAGGTGAGTGAGCCAGAAGGAACTGACCAGCCTTAG   160
GAAGGAACCGTCACAGCTAGGCCATGCTCCAGATATTAATTTCTGAGTCACTGGCCAGGAGCGAGATCCCAGTGTAAGAG   240
TCCCCTGTGATGTAACGTCTGGAAGAATTCCACAGAGAAAGAAGTCAGAAACTTCTACACAGCTGACAGATCAAGATCAC   320
CAGGGCTGTGGGAAGTTTTCTCAGGAGTAAAGTGTGAGGAGTGTGAGGAGCGGAGAGACAGCAGCCCGTGTAAAAGCTGCTGCAGG   400
AGCATGTCTGCAATCTCAGGCCTGGGGGAAGTGAGCAAAGACAGCAGCTGCTGAGAACAAGATGTAGAAAGAACTCTCAGCTTCCT   480
AAGTGCCAAGCTCCAGATTCCGTGGGAGCCCCAGGAATAAGGTGCTTCCCACCATGACAACAACGGACTGAACCTCAGAATCTACAAGTC   560
CAGCATCCTGCTCTGCCCTGCCTTCAAGCTTTGTTTAGTCATGGTGTCTCTTTCACAGCAATGAAAATTCTAAGATAGAAGTTACTAACAAGGAC   640
AGCCCCAATTAAATGTTGTTTAGTCATGGTGTCTCTTTCACAGCAATGAAAATTCTAAGATAGAAGTTACTAACAAGGAC   720
TAGGTATTGCTGTGATGGGCCTGACCATGCTTTCATGGAATAGGGAGGACACATGGTGCTAAGGGTGAACTCTGCGGGTCTGGCTCAGAG   800
GTGGGACTTAATGGGACAGCCTAGTAGGAGGACAGCCTAGTAGGAGGACACATGGAATAGGGAGGACACATGGTGCTAAGGGTGAACTCTGCGGGTCTGGCTCAGAG   880
ATTTCAGAGGAGAATAACTGAGTATGTGGCCTGAGACTGCTTTGTGATACTTTGGTGAGAATGTAGTACTTTTG   960
             M  W  P  G  D  C  F  C  D  T  L  V  R  N  V  G  T  F  C
CCCTCGTTTGAAGTGTCTGCCTGAGGCTCAAGTGAAGACATTCAAATTAATTGCAATGACAGAAGTCTCAGAAAGGGGC  1040
 P  R  L  K  C  L  P  E  A  Q  V  K  T  F  K  L  I  A  M  T  E  V  S  E  K  G  Q
AAGTCCAATCTTCATCATCAGGATATCTTCAATCAGCAACCTCCTCCTGGTGTTTATATACTGCTCTGTATTTATATTCTCTCTCAAGA  1120
 V  Q  S  S  S  G  Y  L  Q  S  A  T  S  K  K  Q  Q  N  S  K  C  N  S  R  N
CAGCAACAGCAGGAAGAGCAGCAGCCACTACCTCCTGCAAATCACATCCCTGCCAGAGCACGAGACAAATCAGTCAGCTGCTGTGG  1200
 Q  Q  Q  E  E  Q  Q  P  L  P  P  L  V  F  F  I  Y  C  S  G  I  Y  I  L  S  Q  E
ATTCCTAGAAATCTACTGTCTTCAGCTGGCAAATCACATCCCTGCCAGAGCACGAGACAAATCAGTCAGCTGCTGTGG  1280
 F  L  E  I  Y  C  L  Q  L  A  N  H  I  P  A  R  A  R  D  K  S  *
ACAATCTGAAGCAGACCACATCCCACCCCTGGAATTAAAAACAAAAACACATTCATAGAACATAACTAGGGGGAAAAAAA  1360
ACCAATACAGTGAGCTTTGAGCTTTGGGATGCCAGTCTTCTTACACGGAGCTCCACAGAGCTCAGAGCTCCACGGTAAGAGAGGGTGGTGGGAGT  1440
GGTGACAGGTAGAAAGACTGTCATCTTTCATGACTGCCTGCATAAGAAGCTAAGCCCCAGGATAGAGAGGCTCAGCCCTCTT  1520
```

Fig. 6-1

```
TATGAAAGAATAGCATGGCTCTAAAAGAACATGTTTAGAGGAAAGACTATTAGAGCCATATTTTGGAAAATATAATGAG  1600
ACACAATATTTTTTGTGAATACAGTTTTATAATAAGGGTGTGTAGCAGGAAATGTCTCCTGACCACCACCTGCTATCCTG  1680
ATGAGGGAACCAGCTGCTATTGGATGCCTGTGGTAAATACCACCCACTTGATGCCATCACTCTGATAGCCCAGACTCA  1760
CTTACACCCCTTCACTGTGCTACTGTTGCCCAGAACCGCCACTATGAGAGGGATTTTTGGTATTACAGCTGCCATTGCAGCCATTATTGCAGTATTACA  1840
GGGGCAACAACPGCTACTGTTGCCCAGAACCGCCACTATGAGAGGCCATCCACATCTTTATGAGGCCTGTCAACGCTGTAGTCTCTAAGTCAGCTGAGGTGC  1920
TACAGGCATAGGAGCTACTAAATCAACATCTTTATGAGGCCTGTCAACGCTGTAGTCTCTAAGTCAGCTGAGGTGC  2000
TGGCTCTTGTTAGGGACATGTGTCTATGGCCTGTGACCCAGGTTTCACTCAAGTTTCACTCTAACCCTTTACCAAGTACATA  2080
ATGCCACTGAAGCCCAACACAGTTGGCTGGTAGATATAACCAGTTCAGACAAATTCCTATTCCTGAAGGCAAGA  2160
AACCACTCACTTGCCCAATTGGTGGTAGATATAACCACGTCCATAACCAACTTTGGAAGCGGAACCAGGCTCCTATG  2240
ACAGAAAGAAGCAGGCTCTTTTTGTCCTTAACCAAATGTGAAGCACAAATGTGAGCACAAATCAAAGCTCCAACAGCAAA  2320
TTCCAAGACATGACATCCTTTTACAGAGTAAAATATTTAAAGACAGAGTCTTCATTCAGAGTCTTCTATTCCCTCCCCCAGGAAGAAA  2400
CTGAACATGACATCCTTTTACAGAGTAAAATATTTAAAGACAGAGTCTTCAGAGTTCAGAGCTCCCCTGTAGGCAGATAATCATGACTCACCACA  2480
CCCTTTAATATTCCGATTAACCTTGATGTGAATCACAGCGCTCCTTCTCCCTGTAGGCAGATAATCATGACTCACCACA  2560
GACCCCTGACTGTGGGCTTCATGTAATTCTGGCAGCAGATAGCATCAGGAAGTGGGGTTGTTGGAAGTGATTAGGTCATAAGG  2640
TACAAAGTCCAGGGATGGACTAGGAGTAACCCTGGAGCAAGCTTTGCACTGTGTATCAAAACAAGACTCCACATTGGGGC  2720
ATCCACACTGAGGCCACCTTGTGAACTAGGCCTCACCTTGGATAAGAAGAAATTGCATTATTTTTACTTTCAAATGTGT  2800
TAAAGAATAAATTTTACTTAAATATATTCTATATTCAATCAGATATGCCCACTGCTGAGACTGAGTATTTGTGTTTTAC  2880
ACCAAAATTTCTTTTGAAACCTAAGCCCTAAGGAGATAGCATCAGGAAGTGGGGTTGTTGGAAGTGATTAGGTCATAAGG  2960
CAGAGTCTTCATAAATAGTATTCTTACTTTGATAAAAGAGATCCAGAGATCCAGAGTTCAATGGCCCCCTACATCAGTGAGGATA  3040
CAGAAAAAGTTGTCAAGGGAGTTTTCCCTGACCCTGCCCACCTGACCATCGAGTTGGGCTCCAGATCCAGATCCAGAACTCTAA  3120
GAACTAAATTCCACTGTGTGATACGGTACCTGGCCAAGGTATTTCAATGTAGAATTTAAAATGGATAAAGACAGCCACT  3200
TCTATGCACAGTTCGAGTTCGAGTGTAAGCATGCTCTACACAGTTAACCACTCTCCATACATTAATGTGGTCTCTACA  3280
CTACTGATAACATAGTAACCACTCTCCATAAACTTAATATGCTCTACACTACTTATACATTGTAACTACTCTCCCGGTA  3360
CAGTTAGTCTACTCTCCACTCTAAAAAGCAGGATGAACATGGGGGAAGTAGCTCTGTCAGTGCATAAAAATGTTT  3440
GCCTTTCGAACCTGAGTTTGATCCCAGAGCCCAACATTGAAAAGGCCATAAAAATCCCAGCACCAC  3520
AGAGGCAGAGACAGCCTCTGATTGACTGACCCTAGTTTAGTCTATGAACTTCAAGCCCATAATTTTGTCTGAAAAAGA  3600
AAGAAAGAAAG                                                                      3611
```

Fig. 6-2

```
DD-10                                                                                      MW
                                                                                           **
OR1a    MLLFERMWIFGLWIWKAVEYFKWGLMGHPSRNMEDFVAGSNLNCVDLAQEISKEKNFRMW

DD-10   PGDCFCDTLVRNVGTFCPRLKCLPEAQVKTFKLIAMTEVSEKGQVQSSSSGYLQSATSKK
        ****  **  **  *****  **   ***  *            *

ORR1a   HKDCFCGILVKNVATFCPCLKSQPEAKVKGIRLIALTKDISKKLSRFVL

DD-10   QQNSKCNSRNQQQQEEQQPLPPLVFIYCSGIYILSQEFLEIYCLQLANHIPARARDKS
```

Fig. 7

INJECTION VOLUME : 10nl / EMBRYO
INJECTION STAGE : 8~16 CELL-STAGE

| | | | TOTAL NUMBER | NORMAL | SECONDARY AXIS | | ABNORMAL GASTRULATION |
|---|---|---|---|---|---|---|---|
| DD-10 | 0.1ng | VV | 9 | 7 (78) | 0 | (0) | 2 (22) |
| DD-10 | 0.1ng | DV | 10 | 10 (100) | 0 | (0) | 0 (0) |
| DD-10 | 1ng | VV | 13 | 4 (31) | 9 | (69) | 0 (0) |
| DD-10 | 1ng | DV | 6 | 5 (83) | 0 | (0) | 1 (17) |
| UNINJECTED | | | 8 | 7 (88) | 0 | (0) | 1 (12) |

Fig. 11

MORPHOGEN-RESPONSIVE SIGNAL TRANSDUCER AND METHODS OF USE THEREOF

REFERENCE TO RELATED APPLICATIONS

The instant application is based on a provisional patent application, U.S. Ser. No. 60/025,311, filed on Sep. 24, 1996 by Express Mail procedure, Mailing Label No. EM 151232298US.

FIELD OF THE INVENTION

This invention relates generally to the field of tissue morphogens and, more particularly, to novel genetic sequences and proteins operative in mammalian tissue morphogenesis.

BACKGROUND OF THE INVENTION

Several novel proteins now have been identified which appear to act as growth or differentiation factors, regulating cell proliferation or differentiation. One group of proteins now has been demonstrated to act as true tissue morphogens, competent to induce the proliferation and differentiation of progenitor cells into functional tissue that is properly vascularized and ennervated. These proteins, referred to herein as "morphogens," includes members of the family of bone morphogenetic proteins (BMPs) which were initially identified by their ability to induce ectopic, endochondral bone morphogenesis. The morphogens generally are classified in the art as a subgroup of the TGF-β superfamily of growth factors (Hogan (1996) *Genes & Development* 10:1580–1594). Members of the morphogen family of proteins include the mammalian osteogenic protein-1 (OP-1, also known as BMP-7, and the Drosophila homolog 60A), osteogenic protein-2 (OP-2, also known as BMP-8), osteogenic protein-3 (OP-3), BMP-2 (also known as BMP-2A or CBMP-2A, and the Drosophila homolog DPP), BMP-3, BMP-4 (also known as BMP-2B or CBMP-2B), BMP-5, BMP-6 and its murine homolog Vgr-1, BMP-9, BMP-10, BMP-11, BMP-12, BMP-13, GDF-5, GDF-6, and GDF-7 (also known respectively as CDMP-1, CDMP-2, and CDMP-3), and the Xenopus homolog Vgl. Members of this family encode secreted polypeptide chains sharing common structural features, including processing from a precursor "pro-form" to yield a mature polypeptide chain competent to dimerize, and containing a carboxy terminal active domain of approximately 97–106 amino acids. All members share a conserved pattern of cysteines in this domain and the active form of these proteins can be either a disulfide-bonded homodimer of a single family member, or a heterodimer of two different members (see, e.g., Massague (1990) *Annu. Rev. Cell Biol.* 6:597; Sampath, et al. (1990) *J. Biol. Chem.* 265:13198).

The members of the morphogen family of proteins are expressed in a variety of tissues during development, as well as in adult tissues. BMP-3 for, example, is expressed in developing human lung and kidney (Vukicevic et al. (1994) *J. Histochem. Cytochem,* 42:869–875), and BMP-4 is expressed in the developing limbs, heart, facial processes and condensed mesenchyme associated with early whisker follicles in embryonic mice (Jones, et al. (1991) *Development* 111:531–542). OP-1 (BMP-7) expression is identified in basement membranes in human embryos, including those of the developing lungs, pancreas, skin, and convoluted tubules of kidneys, ocular tissues, developing brain, and in a variety of developing neural origin tissues (Vukicevic, et al. (1994) *Biochem. Biophys. Res. Commun,* 198:693–700) and WO 92/15323 (PCT/US92/01968). Similarly, Vgr-1, the murine BMP-6 homolog, is expressed most abundantly in adult lung and to a lesser extent, in adult kidney, heart and brain. Some of the morphogens (e.g., OP-2) have not yet been detected in analyses of adult tissues, suggesting only an early developmental role for these morphogens (Ozkaynak, et al. (1992) *J. Biol. Chem.* 267:25220–25227). In contrast, high levels of murine OP-1 expression have been observed in adult mouse kidneys (Ozkaynak, et al. (1991) *Biochem. Biophys. Res. Commun.* 179:116–123). Thus, OP-1 synthesized in the kidney likely can act as a paracrine regulator of bone growth, which would be consistent with the role of the kidneys in both calcium regulation and bone homeostasis. See, for example, WO 92/15323 (PCT/US92/01968, published Mar. 11, 1992) and WO 93/05172 (PCTIUS92/07359, published Mar. 18, 1993).

Two morphogens of particular interest are OP-1 and BMP-4. These proteins, along with their Drosophila homologs, are competent to induce the chondroblastic or osteoblastic phenotype in vitro and to induce endochondral bone formation in vivo, including formation of cartilage, bone and bone marrow, including articular cartilage. Recent studies have revealed that, in general, members of this BMP family have a wide variety of effects not only on bone but on many other cell types, e.g., induction of ventral mesoderm tissues in embryo including renal and adrenal tissues, liver, spleen, pancreas, and skin; induction of neural cells, including retinal cells, cells of the substantial nigra and cerebral cortex, neural cells of central and peripheral nervous system; and initiation of epithelial mesenchymal interactions in tooth development including dentin, cementum and periodontal ligament tissues See, for example, WO 92/15323 (PCT/US92/01968 published Mar. 11, 1992), WO 93/04692 (PCT/US92/07358 published Mar. 18, 1993), WO 94/03200 (PCT/US93/07231 published Feb. 17, 1994), WO 94/06449 (PCT/US93/08808 published Mar. 31, 1993), WO 94/06399 (PCT/US93/08742 published Mar. 31, 1994), and WO 94/06420 (PCT/US93/08885 published Mar. 31, 1994).

The BMP family of proteins are believed to be competent to induce true morphogenesis of mammalian tissue. As a result, significant effort has been devoted to characterizing and developing these and other functionally and structurally related proteins for use in the regenerative healing of injured or diseased mammalian tissues or organs. Particular effort has been devoted to developing morphogen-based therapeutics for the treatment of injured or diseased mammalian bone, dental, periodontal, renal, hepatic and neural tissues, including for example, therapeutic compositions for inducing regenerative healing of bone defects such as fractures, as well as for preserving or restoring healthy metabolic properties in diseased bone tissue, e.g., osteopenic bone tissue. Complete descriptions of efforts to develop and characterize morphogen-based therapeutics for use in mammals, including humans, are set forth in pending U.S. patent application Ser. Nos. 08/404,113, 08/396,930, 08/445,467, 08/152,901, abandoned, Ser. Nos. 08/432,883, 08/155,343, now U.S. Pat. No. 5,656,593, Ser. Nos. 08/260,675, 08/165,541, abandoned, Ser. No. 08/174,605, abandoned, and Ser. No. 07/971,091, abandoned, the teachings of each of which are incorporated herein by reference.

Presently certain complications, however, are encountered during the production, formulation and use in vivo of therapeutic macromolecules, such as morphogen proteins. For example, such proteins are typically produced by fermentation or culture of suitable host cells. Any biological product produced from such host cells for use in humans presently must be shown to be essentially free of host cell contaminants, such as secreted or shed proteins, viral particles or degradation products thereof. Providing such assurance can add significantly to the cost and technical difficulty of commercial production of biological macromolecules. Furthermore, appropriate formulations must be developed for conferring commercially reasonable shelf life on the produced macromolecule, without significant loss of biological efficacy. In addition, useful dosages for administration to an individual need to be determined for each tissue application. For example, in periodontal restoration administering excess BMP2 resulted in bone formation in addition to partial regeneration of periodontium in at least one instance. (Sigurdsson et al. (1995) *J. Periodontal* 66:131–138). An additional complicating factor arises when circumstances warrant an extended course of therapeutic treatment: the treated mammal can develop an immunological response to the macromolecule, and any such response can interfere with effectiveness thereof. In extreme circumstances, treatment must be discontinued.

Accordingly, needs remain for the identification of therapeutically effective analogs of the aforesaid morphogens, particularly for analogs that are inexpensive to produce, are robust upon storage, and have a reduced propensity for eliciting undesirable side effects upon chronic or repeated administration to a mammal.

Objects of the present invention are to (1) provide novel biological markers of tissue morphogenesis including chondrocyte and osteoblast differentiation and bone tissue morphogenesis; (2) provide novel biological markers which appear early in the cascade of events defining morphogen induced morphogenesis; (3) identify novel inducers of morphogenesis that appear downstream of the BMP catalyzing effect; and (4) to provide novel therapeutics derived from these downstream inducers. Still another object of the invention described herein is to provide methods and compositions for identifying a morphogen analog, that is, for identifying a substance that mimics in part or whole a morphogen-induced biological effect in living cells or tissue. Another object of the present invention is to provide an analog identified according to the present identification method. Yet another object is to provide a therapeutic composition comprising an identified analog suitable for administration to a mammal in need thereof, such as a mammal afflicted with a metabolic bone disease, e.g., a disease characterized by osteopenia. Still another object is to provide a bench-mark useful in assessing proper doses of morphogens or analogs thereof.

The foregoing and other objects and features of the invention will be apparent from the description, drawings and claims which follow.

SUMMARY OF THE INVENTION

A novel gene, DD-10, and its encoded polypeptide chain, DD-10, expressed during early onset of morphogen-induced mammalian tissue morphogenesis, now has been discovered. Accordingly, the invention provides (a) a novel biological marker of cell differentiation and tissue morphogenesis, particularly of chondroblast or osteoblast cell differentiation and bone tissue morphogenesis; (b) methods and compositions for screening for and producing morphogen analogs; (c) novel morphogen analogs; (d) downstream inducers of morphogenesis; (e) a novel marker for evaluating morphogen or morphogen analog dosing; and (f) therapeutic methods and compositions using these analogs and/or downstream inducers.

As used herein, the term "morphogen" embraces the class of proteins typified by human osteogenic protein 1 (hOP-1). For ease of description, hOP-1 is recited herein below as a representative morphogen. It will be appreciated by the artisan of ordinary skill in the art, however, that OP-1 merely is representative of the TGF-$\beta$ subclass true tissue morphogenesis, and is not intended to limit the description. Other known, and useful morphogens include, BMP-2, BMP-3, BMP-4, BMP-5, BMP-6, BMP-8, BMP-9, BMP-10, BMP-11, BMP-12, BMP-13, GDF-1, GDF-2, GDF-3.

Accordingly, in one aspect, the present invention features DNA defining an OP-1 responsive gene, the expression product of which is an OP-1 mediated biological effect indicative of a morphogen-induced developmental cascade. Early detection of a DD-10-expression product is predictive of at least osteoblastic differentiation. It has been discovered that within approximately 2–10 hours after exposure to a morphogen such as OP-1, RNA corresponding to the DD-10 gene (nucleotide sequence depicted in SEQ ID No. 1) is detectable and precedes onset of chondroblastic or ostoblastic differentiation. Thus DNA of the present invention corresponds to at least the DD-10 gene nucleotide sequence 1-1264 of SEQ. ID No. 1. and variants thereof, and in certain embodiments corresponds to the entire nucleotide sequence 1-3611 and variants thereof. Additionally, the present invention contemplates a subset of nucleotide sequences located upstream of the DD-10 open reading frame DNA (herein identified as nucleotides 905-1264 of SEQ ID No. 1), which act as upstream regulatory elements to mediate OP-1 responsiveness. That is, certain nucleotide sequences referred to as morphogen responsive transcriptional activating elements govern morphogen-responsiveness of downstream sequences operatively linked thereto. According to the present invention, such upstream regulatory elements correspond at least to nucleotide sequences 121-780, 600-900, or 1-904 of SEQ. ID No. 1 and variants thereof. Furthermore, DNA of the present invention also corresponds to that which hybridizes to the strand complementary to the sequence defined by SEQ. ID No. 1, or any one of the above-recited subsets of sequences, which is inducible by a morphogen such as OP-1 under native conditions.

In another aspect, the present invention features expression products of the above-recited DNA sequences. For example, an isolated polypeptide chain comprising residues of 1–120 of SEQ. ID No. 2 and variants thereof are disclosed herein. Additionally, an amino acid sequence encoded by the nucleotide sequence represented by the DD-10 gene of SEQ. ID No. 1, as well as truncated sequences of the foregoing, inducible by a morphogen such as OP-1 are contemplated herein. The skilled practitioner will also appreciate that RNAs corresponding to any one of the above-recited DNA sequences are an additional feature of the present invention.

As exemplified herein, the present invention contemplates any number of related therapeutic compositions comprising the above-described expression products alone or admixed with carriers or matrices such as those disclosed below. Moreover, in addition to administering compositions comprising DD-10 expression products, the invention contemplates other compositions comprising DD-10 nucleotide sequences as recited above. Furthermore, analogs of DD-10 expression products identified using the methods disclosed herein are contemplated to have therapeutic utility and accordingly can be admixed with suitable matrices and carriers such as those described below.

In a related aspect, the invention provides an isolated binding protein, such as but not limited to an antibody, having binding specificity for a polypeptide chain comprising the amino acid sequence of at least SEQ. ID No. 2. In another related aspect, isolated antisense DNA corresponding to any one of the above-recited nucleotide sequences is featured. Additionally, other aspects of the present invention include an isolated DNA corresponding to any one of the upstream regulatory sequences recited above operatively associated with a reporter gene or gene of interest. Moreover, vectors comprising any one of the above-recited DNAs, including the reporter gene, are contemplated herein. Finally, in a related aspect, a cell transfected with any one of the DNAs or vectors described above are within the scope of the instant invention. Presented below are a variety of non-limiting examples demonstrating administration of any of the foregoing to a mammal for therapeutic considerations.

As will be appreciated by a skilled practitioner, certain of the above-described embodiments can be used to identify substances suspected of having active as a morphogen and/or morphogen analog. Accordingly, in another aspect, the instant invention features an identification method in which a test cell is exposed to at least one candidate compound suspected of having activity as a morphogen or, more preferably, as a morphogen analog. The test cell comprises DNA defining aDD-10 genetic sequence, a DD-10 promoter sequence in operative association with a reporter gene sequence, or sequences derived therefrom. As referred to herein, the DD-10 promoter sequences are selected from the group consisting of: nucleotides 1-904, 600-900 and 121-780, all of SEQ. ID No. 1. The present method further comprises the step of detecting expression of a detectable gene product following exposure of the test cell to the candidate compound. Expression of the detectable gene product indicates that the candidate compound is competent to induct a morphogen mediated biological effect. A morphogen mediated biological effect of particular interest herein comprises the transcriptional activation of OP-1 responsive genes. As referred to herein, expression product includes, but is not limited to, RNAs and polypeptide chains. In certain embodiments, an expression product can be detected within 1–30 hours after exposure to a morphogen such as OP-1, more preferably within 2–10 hours.

As contemplated herein, morphogen analogs are identified by assessing whether candidate substances can mimic a morphogen such as OP-1 by inducing OP-1 mediated expression of an OP-1 inducible gene such as DD-10, and/or by inducing an OP-1 mediated biological effect. In one embodiment, the present invention embraces substances identified according to the methods set forth herein as morphogen analogs. Further, the present invention provides for the production of commercially significant quantities of identified morphogen analogs. Still further, the invention provides for the manufacture and use of DNA comprising a morphogen-responsive signal transducer element.

In certain embodiments, the present method further comprises the steps of contacting an OP-1 responsive cell with a putative morphogen analog identified as described above and detecting whether the analog can induce a biological effect known to be mediated naturally by OP-1 in an OP-1 responsive cell. If desired, this confirming step can be carried out concurrently with the initial identification steps. In other embodiments, the present method further comprises the steps of administering the putative morphogen analog identified as described above to a morphogenically permissive, tissue-specific locus in a mammal and detecting whether the analog can induce tissue-specific morphogenesis at the locus. This confirming step advantageously indicates whether the analog will induce tissue-specific morphogenesis in vivo.

As a result of the present analog identification methods, the invention provides for the production of therapeutic-grade commercially significant quantities of an identified morphogen analog. The invention further provides for production of a derivative of the morphogen analog in which any undesirable properties of the initially identified analog, such as in vivo toxicity or a tendency to degrade upon storage, are mitigated.

Another embodiment provides a method for detecting a morphogen mediated biological affect which comprises the step of detecting an expression product such as those described above. For example, detecting an expression product of the gene defined by SEQ. ID No. 1 is a method of detecting a morphogen mediated biological affect. In one currently preferred embodiment, such method permits detecting chondroblast or osteoblast cell differentiation from a precursor cell type, such as but not limited to, a myoblast cell or a cell of the myoblast/chondroblast/osteoblast lineage. Furthermore, such a method can be used to detect a morphogen mediated biological effect such as but not limited to ventro-vegetal differentiation of a Xenopus embryo. It is contemplated that practice of the instant invention involves detection of RNA and/or polypeptide chains. When practicing such a method, it is contemplated to further comprise the step of providing a morphogen or a morphogen analog, followed by detection of an expression within 1–30 hours, more preferably within 2–24 hours, and most preferably within 2–10 hours of exposure to said morphogen or morphogen analog.

In a related embodiment, the invention features a method for inducing a morphogen-mediated biological response comprising the step of contacting a cell with a DD-10 genetic sequence; a DD-10 expression product, or a DD-10 analog at a concentration and for a time sufficient to induce differentiation of a precursor cell. By way of example only, this embodiment can be practice using a myoblast cell or a cell of the myoblast/chondroblast/osteoblast lineage as the precursor cell whereby said cell can differentiate to a chondroblast or an osteoblast cell.

It will be apparent that the present invention also features a kit for facilitating practice of the above-described methods. In one embodiment, the kit comprises a receptacle for containing a morphogen-responsive test cell comprising a DD-10 DNA sequence. The kit contemplates DD-10 DNA at least corresponding to SEQ. ID No. 1, and in certain embodiments, particularly DNA corresponding to 905-1264, 121-780, 600-900, 1-904, 1264-3611, 1-1264 and 1-3611, all of SEQ. ID No. 1. As will be appreciated by the skilled artisan, such a method can comprise part of a medium or high-flux screening assay. Optionally, the present kits further contain a morphogen and/or a morphogen analog identified according to the present invention.

Still another embodiment contemplates the use of DD-10 as a marker or early bench-mark useful in determining proper morphogen dosing and progression of morphogenesis. For example, when regeneration of non-chondrogenic tissue is desired, induction and detection of DD-10 may reflect a morphogen excess or an overdosing of morphogen. Early appearance of the DD-10 expression product therefore permits dose modification, thereby permitting and/or re-directing the desired morphogenic cascade to occur.

The foregoing and other objects, features and advantages of the present invention will be made more apparent from the following detailed description of preferred embodiments of the invention.

BRIEF DESCRIPTION OF THE DRAWINGS

FIG. 6 shows the nucleotide and deduced amino acid sequences of full length DD-10.

FIG. 7 is a comparison of amino acid sequences of the DD-10 open reading frame and a deduced mouse ORR1 a gene product.

FIG. 11 is a tabular representation of results from an experiment in which Xenopus embryos were microinjected with DD-10 mRNA: VV, ventrovegetal; DV, Dorso-vegetal.

DETAILED DESCRIPTION OF THE INVENTION

Figure 1:
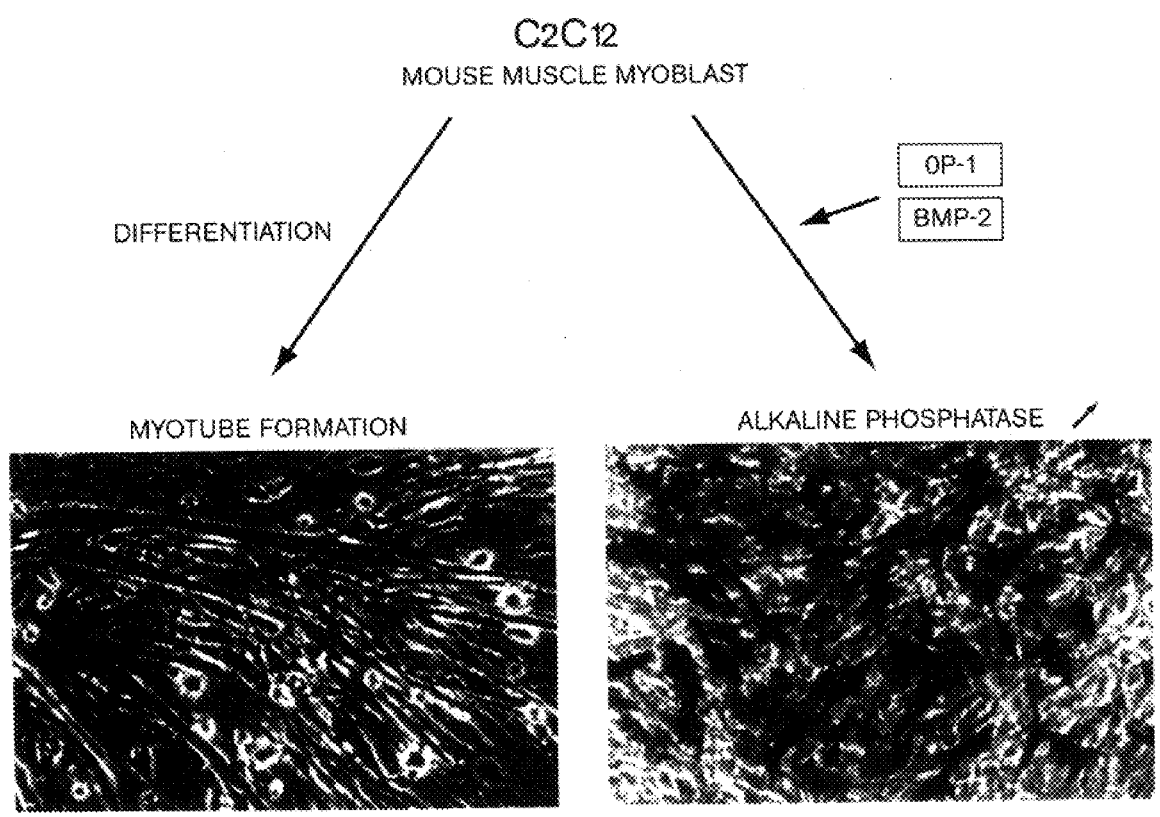
FIG. 1 is a schematic of an autoradiograph of results from an RNA blot analysis demonstrating the induction of alkaline phosphatase synthesis by OP-1 in C2C12 mouse cells.

The invention described herein capitalizes on the discovery that morphogens, including OP-1, can induce expression of certain genes, present naturally in the genome of mammalian cells. That is, stimulation of mammalian cells with OP-1 induces a spectrum of biological effects, including but not limited to the transcriptional activation and subsequent translation of selected cellular genes. As used herein, such genes, whose expression is dependent on morphogen induction or morphogen added exogenously, are referred to as morphogen-responsive signal transducing (downstream) elements. In one embodiment, and by way of example only, the genes also are referred to herein as OP-1-responsive signal transducing (downstream) genes. The present invention exploits the OP-1 responsive properties of this signal transducing element to advantage in a variety of aspects and embodiments as set forth herein. For example, the present invention makes available novel biological markers of tissue morphogenesis, particularly of bone tissue morphogenesis. These novel markers are characterized herein as appearing early in the cascade of events defining morphogenesis, thereby providing a means of ascertaining and monitoring specific events within the cascade.

In a related manner, the present invention permits the skilled artisan to both use and further identify novel inducers of morphogenesis which appear downstream of the BMP catalyzing effect discussed above. Most significantly, the invention exploits their discovery to provide novel therapeutics derived from these downstream inducers, and more preferably, permits identification of therapeutics capable of intervening at specific times during the morphogenetic cascade.

Additionally, the present methods and compositions accordingly exploit the OP-1 responsive properties of the newly-discovered signal transducer element. Generally, the methods and compositions of the present invention provide the skilled artisan with the analytical tools and technical know-how sufficient to identify substances referred to herein as morphogen analogs that can mimic a biological effect mediated by a morphogen such as OP-1. Guidance provided herein accordingly will facilitate evaluation of a variety of diverse substances for morphogen analog properties, thereby broadening the spectrum of potential therapeutic candidates for amelioration and/or treatment of diseases, injuries and deteriorative disorders, especially those related to disruptions and/or abnormalities of developmental and metabolic pathways involved in tissue morphogenesis and tissue repair.

I. Definitions and Currently Preferred Embodiments

In order to more clearly and concisely point out the subject matter of the claimed invention, the following definitions are provided for specific terms used herein in the written description and appended claims.

A morphogen-responsive "signal transducer element" is a cellular product, the expression of which is modulated, for example induced, upon exposure to a morphogen or analog thereof. When a morphogen binds to the surface of a morphogen-responsive cell and thereby elicits an intracellular cascade of biological responses, one such response comprises induction of expression of such a cellular product. An OP-1-responsive signal transducer element is defined similarly. As contemplated herein, a signal transducer element also includes the gene(s), as well as the upstream promoter and/or regulatory sequences associated therewith, encoding the cellular expression product described above. It will be appreciated by the skilled artisan that the element referred to herein as DD-10 is, in one embodiment of the instant invention, an exemplary signal transducer element.

The nucleotide sequence corresponding to DD-10 is set forth in SEQ. ID No. 1. Within the entirety of the sequence (residues 1-3611 of SEQ. ID No. 1), residues 1-904, alternatively residues 121-780 or residues 600-900, correspond to the upstream sequences within which at least one morphogen-responsive transcriptional activating elements occur. It is also contemplated that such elements occur within a shorter nucleotide sequence also corresponding to DD-10 DNA, namely residues 1-1264 of SEQ. ID No. 1. Such morphogen-responsive transcriptional activating elements include nucleotide sequences which are operatively-linked to other nucleotide sequences, particularly those that encode a gene product detectable upon exposure to a morphogen, and which mediate morphogen-responsiveness. Thus, in the instant invention, it is contemplated that the DD-10 expression product detectable upon OP-1 exposure results from at least one such upstream sequence being competent to mediate OP-1 responsiveness. With respect to the DD-10 expression product, it is contemplated to correspond to at least an RNA sequence complementary to the sequence of residues 905-1264 of SEQ. ID No. 1. It is further contemplated to correspond to at least the amino acid sequence encoded by residues 905-1264 and also corresponds to the polypeptide of SEQ. ID No. 2, residues 1-120. As described below, at least residues 905 through 1264 (SEQ. ID No. 1) correspond to the DD-10 open reading frame (ORF). Residues 1265-3611 are referred to herein as the DD-10 downstream sequences. It is further contemplated that equivalents of the above-described DNA sequences are within the scope of the instant invention. That is, equivalent DNA sequences include allelic, species, biosynthetic and degenerate sequences. Degenerate sequences include nucleotide sequences which differ from those recited above but which do not alter the functional and/or biological features associated with and/or resulting from DD-10. Allelic, species and biosynthetic variants include those which differ from the naturally-occurring sequences recited above, but which retain substantially the same functional properties as the DD-10 disclosed and exemplified herein. Finally, the present invention contemplates that DD-10 is a signal transducing element which acts as an intracellular messenger and induces tissue differentiation and tissue morphogenesis, thereby behaving as a morphogen-like agent or analog.

A "morphogen" defines a dimeric protein comprising a pair of polypeptide chains that, when folded, adopt a configuration sufficient for the resulting dimeric protein to elicit morphogenetic responses in cells and tissues displaying receptors having binding specificity for the morphogen. That is, morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of conrnitted cells under appropriate environmental conditions. In particular, the proteins are competent to induce redifferentiation of transformed cells or cells which otherwise have deviated from their normal differentiation pathway.

Morphogens, as also defined herein, induce or reinduce mammalian cells, particularly uncommitted progenitor cells, to undergo a fully integrated developmental cascade of biological and molecular events that culminate in the morphogenesis of fully differentiated, functional tissue of a type appropriate to the context or local biological environment in which morphogenesis is induced, including any vascularization, connective tissue formation, ennervation and the like characteristic of tissue naturally-occurring in such a context. For example, if cells are stimulated by OP-1 in the context of nerve, bone or liver tissue, the resulting cascade of morphogenesis culminates in the formation of new or regenerative differentiated tissue appropriate to the selected local environment. Morphogenesis therefore differs significantly from simple reparative healing processes in which scar tissue (e.g., fibrous connective tissue) is formed and fills a lesion or other defect in differentiated, functional tissue.

Further, morphogenesis as contemplated herein occurs in a "permissive environment" by which is meant a local environment that does not stifle or suppress morphogenesis (e.g., tissue regeneration or regenerative healing). Other components of a permissive environment typically include signals, e.g., cell surface markers or extracellular secreted substances, that direct the tissue specificity of differentiation. Permissive environments exist, e.g., in embryonic tissue or in wounded or diseased tissue, including tissue subjected to surgical intervention. Often, a permissive environment comprises a suitable matrix or substratum to which cells undergoing differentiation can anchor. Such matrices can constitute endogenous tissue or extracellular matrix material, or they can be formulated synthetically. In one embodiment, exemplary synthetic matrices comprise tissue-specific structural components, e.g., collagen or glycosaminoglycans of the same types as occur naturally in the desired tissue. It will be appreciated that tissue-specific components need not be provided exogenously provided such components are present at the defect locus. See, for example, WO 94/03200 (PCT/US93/07231 published Feb. 17, 1994) for additional teachings on useful matrices.

A morphogen as isolated from natural sources in mature, biologically active form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. The reduced polypeptide subunits themselves have no detectable morphogenic activity. Glycosylation, however, is not required for biological activity. The unglycosylated protein has an apparent molecular weight of about 27 kDa. When reduced, the 27 kDa protein gives rise to two unglycosylated polypeptide subunits having molecular weights of about 14 kDa to 16 kDa. The polypeptides which together form the biologically active dimer comprise at least six, preferably at least seven, positionally conserved cysteine residues as set forth in WO 92/15323 (PCT/US92/10968 published Sep. 17, 1992), the teachings of which have been incorporated herein by reference.

As stated above, the representative morphogen, for purposes of the present invention, comprises an OP-1 or an OP-1-related polypeptide. Sequences of useful OP-1 polypeptides are recited in U.S. Pat. Nos. 5,011,691; 5,018,753 and 5,266,683; in Ozkaynak et al. (1990) *EMBO J* 9:2085–2093; and Sampath et al. (1993) *Proc. Natl. Acad. Sci. USA* 90: 6004–6008. Additional useful sequences occur in the C-terminal domains of DPP (from Drosophila), Vg1 (from Xenopus), 60A (from Drosophila, see Wharton et al. (1991), *Proc. Natl. Acad. Sci. USA* 88:9214–9218), Vgr-1 (from mouse), the OP-1 and OP2 proteins, (see U.S. Pat. No. 5,011,691 by Oppermann et al.), as well as the proteins referred to as BMP2, BMP3, BMP4 (see W088/00205, U.S. Pat. No. 5,013,649 and W091/18098), BMP5 and BMP6 (see W090/11366, PCT/US90/01630) and BMP8 and 9. Each of the foregoing polypeptides, when oxidized and dimerized, is useful as a morphogen herein. Further, this family of morphogenic proteins includes longer forms of a given protein, as well as phylogenetic, e.g., species and allelic variants and biosynthetic mutants thereof, including addition and deletion mutants and variants, such as those which can alter the conserved C-terminal cysteine skeleton, provided that the alteration still allows the protein to form a dimeric species having a conformation capable of inducing morphogenesis, e.g., endochondral bone formation when implanted in a mammal in conjunction with a matrix permissive of bone morphogenesis. In addition, morphogens useful in this invention can include forms having varying glycosylation patterns and varying N-termini, can be naturally occurring or biosynthetically derived, and can be produced by expression of recombinant DNA in procaryotic or eucaryotic host cells according to established techniques. The proteins are active either as homodimers or heterodimers.

Morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. The term "progenitor cells" includes uncommitted cells, preferably of mammalian origin, that are competent to differentiate into one or more specific types of differentiated cells, depending on their genomic repertoire and the tissue specificity of the permissive environment in which morphogenesis is induced. Pluripotent cells and partially differentiated cells both are contemplated. Preferably, morphogenesis culminates in the formation of differentiated tissue having structural and function properties of a tissue that occurs naturally in the body of a mammal. As noted above, morphogens that induce proliferation and differentiation at least of mammalian bone progenitor cells, and/or support the formation, growth, maintenance and functional properties of mammalian endochondral bone tissue, are of particular interest herein.

In general terms, an "analog" is understood to be a functional equivalent of a given substance and can be a substitute for said substance, including as a therapeutic substitute. An analog also can be a structural equivalent. As used herein, a "morphogen analog" is a substance that mimics a biological effect induced and/or mediated by a morphogen, such as OP-1. Any substance having such mimetic properties, regardless of the chemical or biochemical nature thereof, can be used as a morphogen analog herein. The present morphogen analog can be a simple or complex substance produced by a living system or through chemical or biochemical synthetic techniques. It can be a substance that occurs in nature or it can be a novel substance, e.g., prepared according to principles of rational drug design. It can be a substance that structurally resembles a solvent-exposed morphogen surface epitope implicated in receptor interactions, a substance that otherwise stimulates a morphogen receptor displayed on the surface of a morphogen responsive cell, or a cell-membrane permeant substance or otherwise intracellular acting molecule that interacts with an intracellular component of the signal transduction machinery of a morphogen responsive cell and thereby stimulates a morphogen specific biological effect. Such intracellular acting morphogen analogs also are referred to herein as "downstream morphogenesis inducers". As used herein, a morphogen analog can be referred to as a "mimic" or a "mimetic".

In one embodiment, the morphogen-responsive signal transducer element referred to herein as DD-10, and its encoded protein, act as an intracellular morphogen analog. Thus, in another embodiment, morphogen analogs include functional analogs, equivalents or mimetics of DD-10. It will be understood from the teachings set forth herein, including for example Examples 10–13, that administration of DD-10 or analogs thereof can result in tissue differentiation and/or tissue morphogenesis. Also contemplated herein are amino acid variants of DD-10, including allelic or species variants thereof or other naturally-occurring or biosynthetic amino acid sequence variants. As used herein, an amino acid sequence variant comprises a polypeptide having an amino acid sequence which differs from the naturally-occurring sequence, yet which retains substantially the same functional properties as the DD-10 described and exemplified herein.

In another embodiment, the morphogen analog enabled by the present invention comprises a candidate compound or an agent which acts as an agonist of a morphogen receptor. An "agonist" of a receptor means a compound which binds to the receptor and for which such binding has a similar functional result as binding of a morphogen to the receptor. That is, the compound upon interaction with the receptor, produces the same or a substantially similar transmembrane and/or intracellular effect as a morphogen. Thus, an agonist of a morphogen receptor binds to the receptor and such binding has the same or a similar functional result as morphogen binding (e.g., induction of morphogenesis). The activity or potency of an agonist can be less than that of the natural morphogen, in which case the agonist is said to be a "partial agonist," or it can be equal to or greater than that of the natural ligand, in which case it is said to be a "full agonist." Thus, for example, a small peptide or other molecule which can mimic the activity of a morphogen in binding to and activating the morphogen's receptor can be employed as an equivalent of the morphogen. Preferably the agonist is a full agonist, but partial morphogen receptor agonists can also be advantageously employed. Methods of identifying such agonists are disclosed herein and include assays for compounds which induce morphogen-mediated responses (e.g., induction of differentiation of metanephric mesenchyme, induction of endochondral bone formation, and the like). Such an agonist also can be referred to as a morphogen "mimic," "mimetic," or "analog."

Also by way of example and without being limited hereto, another type of morphogen analog enabled by the present invention can be prepared through judicious application of the principles of biosynthetic antibody binding site (BABS) technology as set forth in U.S. Pat. Nos. 5,132,405, 5,091,513 and 5,258,498, the teachings of which are incorporated herein by reference. BABS analog constructs can be prepared from antibodies, preferably produced by hybridoma cells, that bind specifically to a morphogen cell surface receptor. Alternatively, BABS analysis can be prepared from anti-idiotypic antibodies specifically reactive with the antigen binding site of an antibody that blocks morphogen biological activity. Vukicevic et al. (1994) *Biochem. Biophys. Res. Comm.* 198:693–700 teaches the preparation of OP-1 specific monoclonal antibodies. Skilled artisans will appreciate that such antibodies can be used as immunogens in the routine preparation of anti-idiotypic antibodies from which BABS analogs of the present invention can be prepared.

A structurally distinct class of morphogen analogs, again set forth herein for illustration and not for limitation, can be prepared through application of the principles of directed molecular evolution as set forth in Tuerk et al. (1990) *Science* 249:505–510, Famulok et al. (1992) *Angew. Chem. Intl. Ed. Engl.* 31:979–988 and Bock et al. (1992) *Nature* 355:564–556, the teachings of each of which are incorporated by reference herein. The directed molecular evolution process involves isolation of a nucleic acid molecule, typically an RNA, that binds with high affinity to a selected ligand such as a protein. Such a nucleic acid molecule is referred to in the art as an "aptamer." The desired aptamer is initially present in a random pool of nucleic acid molecules, and is isolated by performing several rounds of ligand-affinity based chromatography alternating with PCR-based amplification of ligand-binding nucleic acids. Bock et al. (1992), above, have demonstrated the preparations of aptamers, suitable for in vivo use in mammals, that specifically inhibit the blood clot promoting factor, thrombin. As contemplated herein, such aptamers can be derived from a morphogen or from DD-10.

Yet another structurally distinct class of morphogen analogs can be prepared by selecting appropriate members of a random peptide library (Scott et al. (1990) *Science* 249:386–390) or a combinatorially synthesized random library of organic or inorganic compounds (Needels et al. (1993) *Proc. Natl. Acad. Sci. USA* 90:10700–10704; Ohlmeyer et al. (1993) *Proc. Natl. Acad. Sci. USA* 90:10922–10926). Skilled artisans will appreciate that the foregoing and other related technologies, taken together with long-established principles of screening biologically-produced substances, offer a wide array of candidate substances for screening for morphogen analog activity. As enabled by this disclosure, the product of such a library screen can mimic OP-1 or another morphogen as a ligand for morphogen receptor binding. Alternatively, the product can mimic DD-10 and induce a morphogen-specific biological effect through one or more intracellular interactions.

Thus, a naturally-sourced OP-1 or other morphogen analog, including a DD-10 analog or mimetic, can comprise a polypeptide, polynucleotide, carbohydrate, lipid, amino acid, nucleic acid, sugar, fatty acid, steroid, or a derivative of any one of the aforementioned compounds. It can be an intermediate or end product of metabolism of a eukaryotic or prokaryotic cell. Alternatively, the analog can be a biological response modifier or a toxin.

For ease of practice of the invention set forth herein, a kit is provided for screening candidate substances for morphogen mimetic properties and DD-10 mimetic properties, as is a kit for preparing a cell for the inducible production of a gene product. The kits herein comprise a receptacle for containing DNA, and DNA comprising a morphogen-responsive signal transducer element, corresponding to DD-10 DNA. Said DD-10 DNA corresponds to the nucleotide sequence in SEQ. ID No. 1. Said DD-10 DNA further corresponds to nucleotide sequences selected from the group consisting of: 905-1264; 121-780; 600-900; 1-904; 1264-3611; 1-1264; 1-3611, all of SEQ. ID No. 1. In certain embodiments, the kits further comprise a morphogen-responsive test cell comprising at least any one of the above-recited DD-10 preferred nucleotide sequences. Optionally, the DNA comprises a reporter gene encoding a detectable gene product. Certain other kits contain a morphogen and/or a compound identified by the methods of the instant invention as morphogen analogs. Practice of the above-described embodiments is exemplified in at least Example 8 set forth herein.

Thus, a morphogen analog identified according to the method of the present invention is a substance that functionally mimics a morphogen by inducing at least one "morphogen-mediated biological effect" in a morphogen-responsive cell or tissue. The effect can be any biological effect resulting from exposure to or contact with a morphogen, including but not limited to the induction of tissue-specific morphogenesis. Morphogen-mediated biological effects include cellular and molecular responses to morphogen exposure, e.g., as described in Ser. No. 08/115,914, abandoned, Ser. No. 08/155,343, now U.S. Pat. No. 5,656,593, Ser. Nos. 08/260,675, 08/165,541 abandoned, and 08/174,605, abandoned, the disclosures of which have been incorporated herein by reference. It will accordingly be appreciated that an "OP-1 mediated biological effect" is any biological effect resulting from exposure to or contact of morphogen-responsive cells or tissue with OP-1, whether in vitro or in vivo. An OP-1 mediated biological effect of particular interest herein includes stimulation of the expression of one or more specific gene(s), including stimulation of the binding of an intracellular substance to DNA expression regulation elements. Other OP-1 mediated biological effects include stimulation of cellular proliferation, cellular differentiation, maintenance of a differentiated phenotype, and, under the appropriate circumstances, induction of redifferentiation. Further preferred OP-1 mediated biological effects are molecular or biochemical effects associated with tissue-specific morphogenesis, e.g., endochondral bone formation or nerve regeneration.

Specific morphogen mediated biological effects associated with endochondral bone formation include induction of mitogenesis and phenotypic markers for chondrocyte and osteoblast differentiation in fetal rat calvaria cells. Known useful induced phenotypic markers include types I, II and X collagen; alkaline phosphatase; and osteocalcin. It now has been discovered that DD-10 is induced in response to morphogen stimulation. Thus, a candidate compound identified as a morphogen analog using the methods and compositions of the instant invention can mimic a morphogen, e.g., OP-1, by inducing at least one of the foregoing biological effects.

As disclosed herein, DD-10 is a novel marker of chondroblast or osteoblast differentiation induced in response to morphogen stimulation. In accordance with this observation, DD-10 can be used as a diagnostic tool to measure morphogen dosing as well as the progression of morphogen-induced tissue repair. For example, if a morphogen or analog thereof is administered for non-chondrogenic tissue repair, DD-10 can be used to assess, early in the course of morphogenesis, whether an osteoblastic phenotype is stimulated, thereby indicating perhaps a dosing excess. Cells at the site of tissue repair can be collected, for example, by scraping followed by in situ hybridization or histochemical analysis using DD-10-specific reagents as described herein below. Detection of a DD-10 expression product is indicative of chondroblastic or osteoblastic differentiation occurring at the repair site. If appropriate, the dose can thereafter be modified to direct or re-direct the course of tissue differentiation at the site. As will be appreciated by the skilled artisan, this is merely illustrative of a variety of diagnostic applications for DD-10 as an indicia of morphogen or morphogen analog dosing.

As used herein, an "OP-1 responsive cell" is any cell that displays a receptor on its surface to which OP-1 binds to induce an intracellular OP-1 mediated biological effect. A morphogen responsive cell is herein defined similarly. That is, "morphogen-responsive" means a cell which displays a receptor to which a morphogen can bind and induce an intracellular morphogen-mediated biological effect. The induced intracellular biological effect is characteristic of morphogenic biological activity, such as activation of a second messenger cascade of events involving for example, cyclic nucleotides, diacylglycerol, and/or and other indicators of intracellular signal transduction such as activation or suppression of gene expression, including induction of mRNA resulting from gene transcription and/or induction of protein synthesis resulting from translation of mRNA transcripts indicative of tissue morphogenesis. Exemplary OP-1 responsive cells are preferably of mammalian origin and include, but are not limited to, osteogenic progenitor cells; calvaria-derived cells; osteoblasts; osteoclasts; osteosarcoma cells and cells of hepatic or neural origin. Any such OP-1 or morphogen responsive cell can be a suitable test cell for assessing whether a candidate substance is a morphogen analog.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism.

Practice of the invention, including additional preferred aspects and embodiments thereof, will be still more fully understood from the following examples, which are presented herein for illustration only and should not be construed as limiting the invention in any way.

II. Discovery, Identification and Characterization of Novel Morphogen-Responsive Signal Transducers and Methods of Use Thereof

EXAMPLE 1

OP-1 Stimulates Alkaline Phosphatase Activity in C2C12 Mouse Myoblast Cells

OP-1 responsiveness was examined in the mouse myoblast cell line C2C12 (ATCC CRL 1772), which differentiates to form myotubes under reduced serum concentration (see Blau, H. M. et al. (1983) X11 32:1171–80; and, Katagiri, T. et al., (1994) *Journal of Cell Biology* 127(6): 1755–1766.). Briefly, C2C12 cells were plated in 6-well culture plates in Dulbecco's Modified Eagle Medium (DMEM) (Gibco, Long Island, N.Y.) with 15% fetal calf serum (Gibco) and allowed to grow to confluency. Medium was replaced with DMEM containing 5% fetal calf serum in the presence (FIG. 1, right panel) and absence (FIG. 1, left panel) of 300 mg/ml OP-1 (Creative Biomolecules, Inc. Hopkington, Mass.). OP-1 induced alkaline phosphatase in C2C12 cells by 48 h with high levels detected by six days after routine fixation and staining for alkaline phosphatase activity using papthol AS-MX phosphate and fast blue BB salt. In contrast, C2C12 cells not treated with OP-1 underwent myotube formation under the same low serum culture conditions.

These observations indicate that C2C12 cells provide a useful cell culture method for assessing whether test substances function as morphogen analogs as well as for further delineating one or more of the biological mechanisms associated with morphogen-induced biosynthesis or differentiation of such cells. In particular, C2C12 cells provide a useful cell line for the identification of novel morphogen responsive genes as discussed herein below. Inasmuch as morphogens, by definition, participate in a cascade of cellular events that lead to conditions as diverse as cell proliferation, differentiation, apoptosis, cell-fate determination, and morphogenesis, it is likely that morphogens, including OP-1, induce the biosynthesis of a number of other factors that participate in these processes (e.g., additional morphogens or morphogen analogs). Those skilled in the art will appreciate that the general principles and parameters of the C2C12-based in vitro model system, including monitoring the expression of phenotypic markers such as alkaline phosphatase, have been exploited in other cell culture systems. See, e.g., Manduca et al. (1992) *Cell Biology* 57:193–201 for a description of a chick embryo osteoblast in vitro assay system; Reginato et al. (1993) *Dev. Dyn.* 198:284–295 for a description of a chick embryonic sternum system; Asahina et al. (1993) *J. Cell Biology* 123:921–933 for a description of an in vitro system using primary cultures of newborn rat calvaria.

Figure 2:
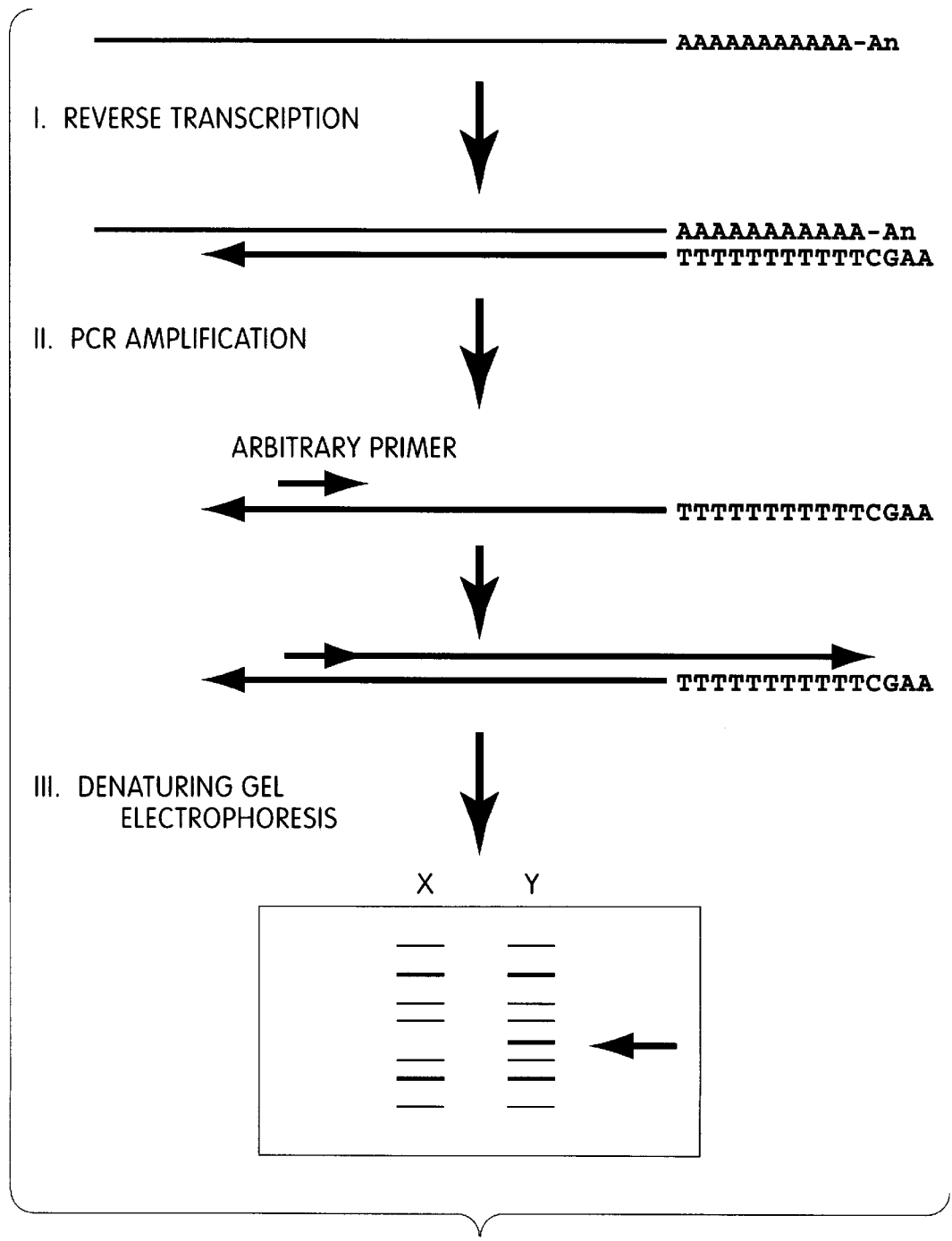
FIG. 2 is a schematic representation of the protocol for mRNA Differential Display.

EXAMPLE 2
A Novel Gene Product, DD-10, Induced by OP-1 Is Identified Using Differential Display A novel mRNA was identified in C2C12 cells by examining increased mRNA levels after morphogen (OP-1) treatment relative to those in unstimulated cells using the Differential Display technique (Liang, P. and Pardee, A. B. (1992) *Science* 257:967–71, the disclosure of which is herein incorporated by reference). Briefly, Differential Display is a polymerase chain reaction (PCR)-based technique which uses a set of oligonucleotide primers, one being anchored to the polyadenylate tail of a subset of mRNAs, the other being short and arbitrary in sequence so that it anneals at different positions relative to the first primer. The mRNA subpopulations amplified by these primers after reverse transcription are resolved on a DNA sequencing gel. The PCR products resemble a discontiguous DNA ladder, the presence or absence or variation in intensity of particular bands representing the relative quantity of particular mRNA species (FIG. 2). The appearance of new bands (e.g., in the products of C2C12 cells after treatment with OP-1) suggests the induction of corresponding mRNAs.

Figure 3:
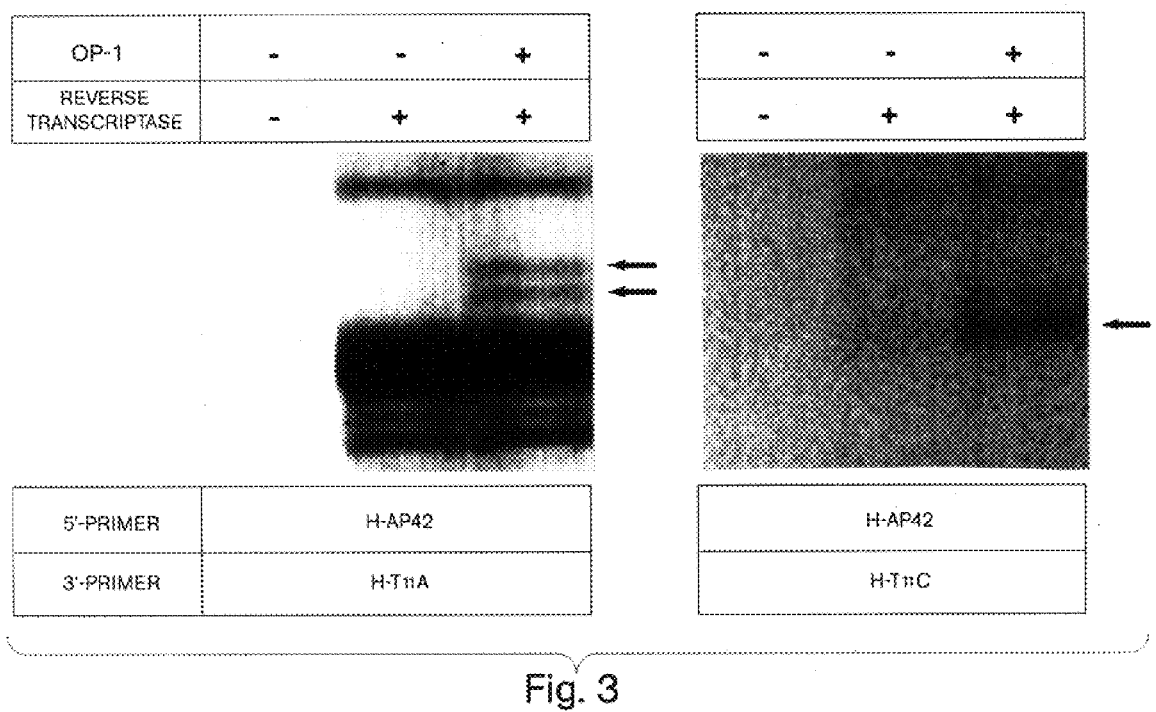
FIG. 3 is a representative view of differentially amplified PCR products for unstimulated and OP-1 stimulated C2C12 cells.

OP-1 treated C2C12 cells provide a useful model for the identification of novel genes responsive to OP-1 or other morphogens by Differential Display. Briefly, C2C12 cells were cultured in DMEM containing 15% FCS until they reached confluency. The serum concentration was reduced to 5% and cells were allowed to grow in the presence or absence of 300 ng/ml OP-1 for 2 h. Messenger RNAs were extracted by standard methods, reverse transcribed into first strand cDNA and used in the PCR-based differential screening using various primers as described above. The amplified cDNAs were separated on a 6% sequencing gel (FIG. 3). The "positive" bands, so named because they were seen only in the PCR products from OP-1 treated cells, were excised from the gel, re-amplified by the same sets of PCR primers and subcloned into pGEM-T vector DNA (Promega).

Figure 4:
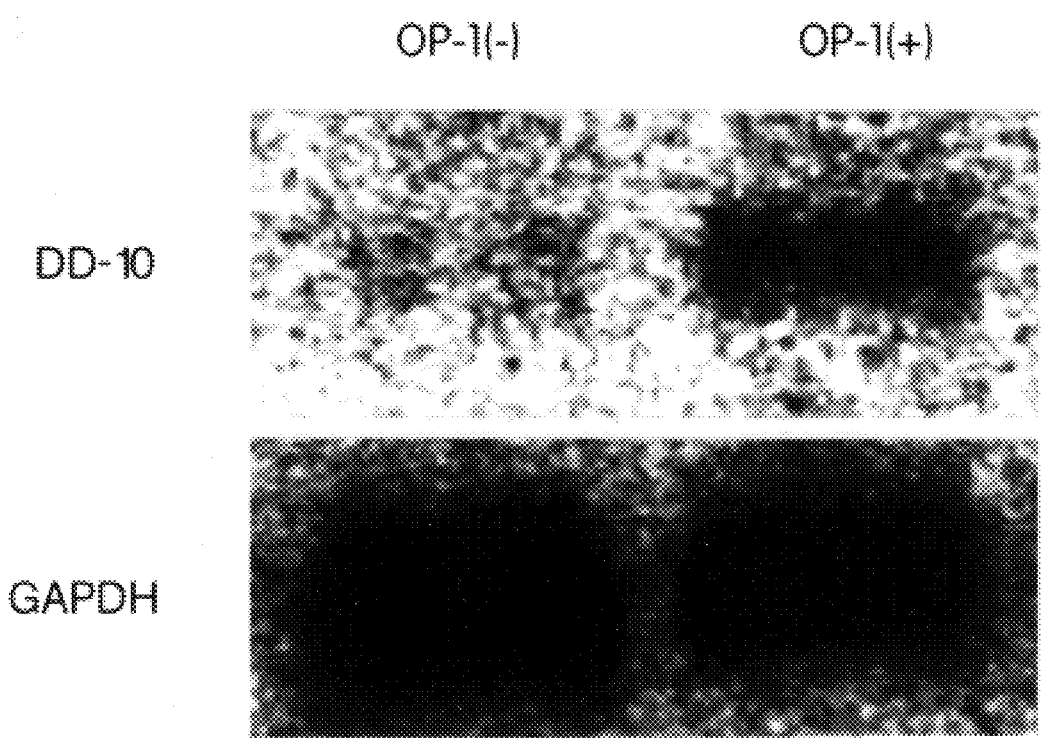
FIG. 4 is a schematic of an autoradiograph of results from an RNA blot analysis demonstrating the induction of DD-10 mRNA in C2C12 cells.

Based on the above experiments, a cDNA clone, termed DD-10, was isolated which was reproducibly observed only in the mRNA derived from morphogen (OP-1) treated cells. In order to confirm these results, DD-10 was used in accordance with art-recognized techniques to probe a northern blot containing mRNA from untreated cells and from cells which were treated with OP-1 for 2 hours. The DD-10 cDNA used to probe the Northern blot membrane was radiolabelled according to standard techniques. OP-1 caused a dramatic induction of a 3 Kb transcript corresponding to DD-10 mRNA by 2 h post treatment (FIG. 4).

EXAMPLE 3
Cloning of Full Length DD-10 cDNAs and Genes

Figure 5:
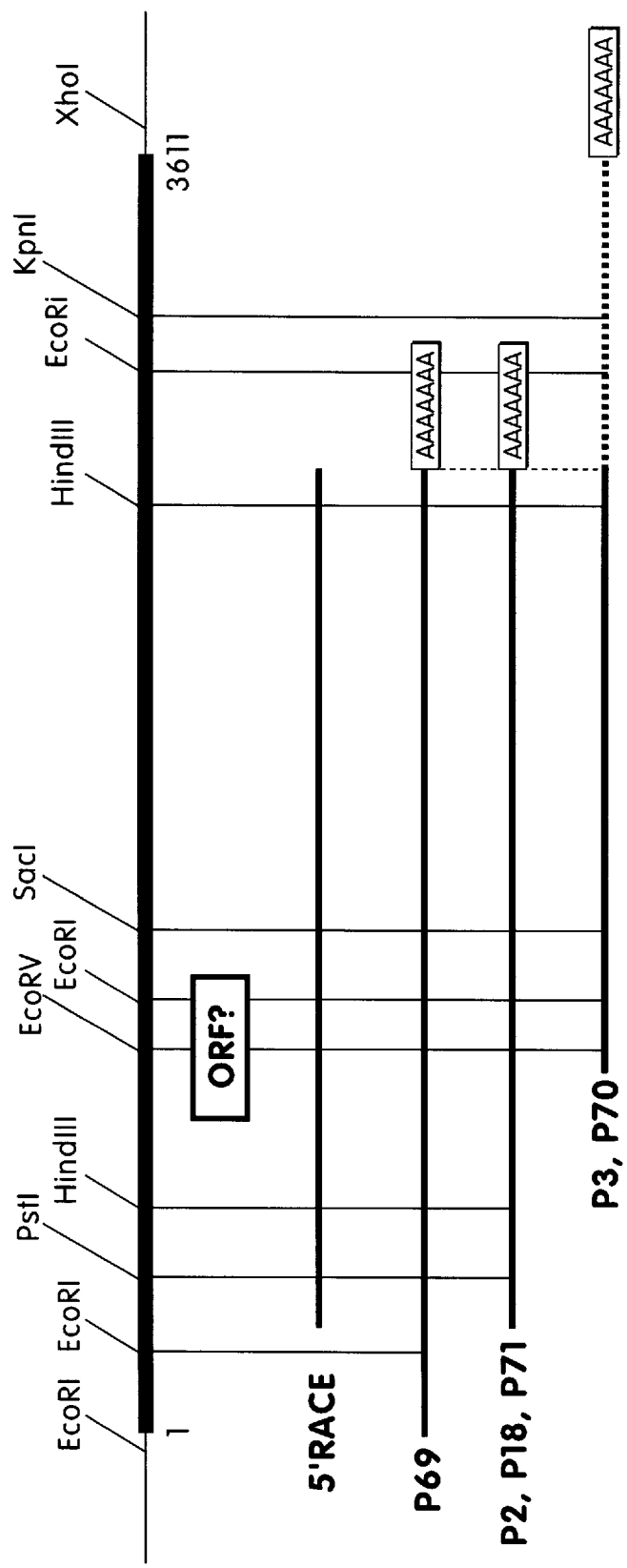
FIG. 5 is a schematic representation of the partial cDNA clones isolated from an OP-1 treated C2C12 cell cDNA library.

In order to obtain a full length DD-10 cDNA sequence, a mouse cDNA library was created from the mRNA of OP-1 treated C2C12 cells and probed with the partial DD-10 cDNA using routine methods. Several overlapping clones were obtained and their sequences were confirmed on both strands (FIGS. 5 and 6; and, residues 1-3611 of SEQ. ID No.1). An amalgamation of the results produced therein revealed the presence of a putative open reading frame (ORF) (corresponding to nucleotide residues 905–1264 of SEQ. ID No. 1), 120 amino acids in length (corresponding to the amino acids encoded by nucleotides 905-1264 of SEQ. ID No. 1), and the presence of two alternative polyadenylation sites. The amino acid sequence encoded by the putative ORF (nucleotides 905–1264 of SEQ. ID No. 1) were found to contain a limited sequence which currently appears similar to the mouse ORR1a cDNA which is reportedly a transposon-like element encoding a protein of unknown function; the nucleic acid sequence encoding this protein corresponds to Genebank accession number: MMO 17092, the disclosure of which is herein incorporated by reference (FIG. 7).

To obtain the corresponding DD-10 gene, a genomic mouse library such as any one of those available commercially, can be probed with the full length DD-10 cDNA. It is expected that the DD-10 gene can be obtained and isolated, and its sequence determined. Furthermore, genomic DD-10 clones containing an upstream promoter sequence(s) are useful for promoter analyses which can be used to identify and study the mechanisms involved in OP-1 signal transduction, as well as to construct a transfectant cell line useful for the identification of other OP-1 responsive genes, as discussed herein below.

The above-described identification of mouse DD-10 mRNA in C2C12 myoblast cells allows DD-10 transcripts to be identified in other species. For example, the DD-10 sequence itself can be used as a probe or the sequence can be modified to account for a preferred codon bias (e.g., human codon bias) and used to probe cDNA or genomic libraries prepared from, e.g., humans, Drosophila, Xenopus, zebra fish, or rats. These DD-10 homologs can be used in the same manner as is described below for mouse DD-10, i.e., as markers for OP-1 activities and to identify novel morphogen analogs.

Probes based on the nucleic acid sequence of DD-10 are synthesized on commercially available DNA synthesizers, e.g. Applied Biosystems model 381A, using standard techniques (e.g. in: Gait, *Oligonucleotide Synthesis: A Practical Approach,* IRL Press, Washington D.C., 1984). It is preferable that the probes are at least 8–50 bases long, more preferably 18–30 bases long. Probes are labeled in a variety of ways standard in the art, e.g. using radioactive, enzymatic or colorimetric labels as described, for example, by Berent et al, (Can/June 1985) *Biotechniques:* 208–220; and Jablonski et al, (1986) *Nucleic Acids Research* 14: 6115–6128.

Preferably, low stringency conditions are employed when screening a library for DD-10 homologs. Preferred DD-10 specific probes are those corresponding to bases conserved between the known DD-10 and yet-to-be identified other similar sequences. Useful probes can be designed from bases corresponding to amino acids 1–31 of DD-10, for example (see FIG. 7). The probe can be further modified to use a preferred species codon bias.

For example, for a probe of about 20–40 bases a typical prehybridization, hybridization, and wash protocol is as follows: (1) prehybridization: incubate nitrocellulose filters containing the denatured target DNA for 3 hours at 55° C. in 5X Denhardfs solution, 6X SSC (20X SSC consists of 175 g NaCl, 88.2 g sodium citrate in 800 ml $H_2O$ adjusted to pH. 7.0 with 10N NaOH), 0.1% SDS, and 100 mg/ml denatured salmon sperm DNA, (2) hybridization: incubate filters in prehybridization solution plus probe at 42° C. for 24 hours, (3) wash; three 15 minutes washes in 6X SSC and 0.1% SDS at room temperature, followed by a final 1 minutes wash in 6x SSC and 0.1% SDS at 55° C. Other equivalent procedures, e.g. employing organic solvents such as formamide, are well known in the art.

Alternatively, DD-10 specific DNA can be amplified using a PCR methodology such as the one described below, to amplify approximately 500 base pair fragments. As for the hybridization screening probes described above, the primer sequences preferably are derived from sequences from conserved or other preferred domains. In one preferred embodiment, the primer sequences are derived from the open rendering frame defining the amino acid sequence presented in FIG. 6.

Oligonucleotides are prepared with degeneracies introduced to include multiple probable sequences encoding the DD-10 amino acid sequence, while maintaining the preferred species codon bias. In addition, where possible, observed conserved nucleotide sequences are exploited.

These primers then are used in a PCR reaction using mRNA or genomic DNA of species of interest and standard procedures well known in the art, see for example, Saiki et al. (1985) *Science* 230:1350–1354.

Briefly, degenerate oligonucleotides are synthesized on a standard automated DNA synthesizer, (e.g., Applied Biosystems Model 381A) following manufacturer's instructions, and then purified using standard procedures.

PCR reactions are performed with a commercially available thermal cycler and reagent kit (e.g., GeneAmp, Perkins & Elmer Corp., Norwalk) and following the manufacturer's instructions in a standard PCR protocol: in a 100 µl final volume with 1 µg genomic DNA, 1 mM final concentration of each primer, 0.2 mM dNTP's, 50 mM KCl, 10 mM Tris-HCl pH 9.0, 0.1% Triton X-100, 1.5 mM $MgCl_2$, 2.5 units of Taq polymerase. The reaction mixture is heated to 60° C. before addition of the nucleotides and polymerase and amplification is performed for 40 cycles:

program: 94° C. 1 min
55° C. 1 min. 30 sec.
72° C. 1 min. 20 sec. + 1 sec followed by a single extension of 72° C. 5 min.
4° C. hold Amplified products then are separated by standard polyacrylamide gel electrophoresis, and fragments of the appropriate size (e.g., 300–500 bases) excised and purified using standard procedures. These fragments then are subcloned into a standard, commercially available cloning vector (e.g., available from Invitrogen Inc., San Diego) compatible with the PCR-generated DNA fragment ends. DNA from individual clones then is prepared by standard alkaline lysis and the isolated DNAs sequenced using standard procedures and commercially available reagents (e.g., dideoxy sequencing, U.S. BioChem Sequencing Kit, Cleveland, Ohio)

PCR amplified DNAs can then be used to create a probe (by random priming) for the screening of cDNA or genomic libraries of a species of interest under higher stringency conditions (e.g., washed at 0.1X SSC, 0.1% SDS, at 50° C.) to identify the complete coding sequences or genes using standard library screening procedures (see, for example, Maniatis, *Molecular Cloning: A Laboratory Manual* (2nd Ed'n, (1989) Cold Spring Harbor, N.Y.). Using standard probing procedures and appropriate hybridization conditions, homologs and other DD-10 variants can be identified, including species variants such as the human DD-10 homolog, allelic variants, and closely related analogs.

The invention also provides means for isolating transcriptional regulatory elements, particularly those occurring 5' and 3' to the coding sequence, as well as other, nontranslated sequences affecting stability, processing, transcription, polyadenylation, translation, tissue specificity, and intracellular routing and localization of the RNA molecule. For example, using PCR primers derived from the 5' terminus of the sequence of SEQ. ID No. 1, such as a sequence corresponding to nucleotide residues 1-904 or 121-780 or 600-900 of SEQ. ID No. 1, upstream promoter or mRNA untranslated sequences can be obtained. It is herein contemplated that morphogen responsive transcriptional activating elements can exist within the nucleic acid sequences upstream of the DD-10 ORF, such as for example within the promoter of the DD-10 gene, which play a role in modulation of DD-10 expression at the RNA and/or protein level. Sequences such as those corresponding to nucleotides 1-904, 121-780 and/or 600-900 are contemplated to have regulatory significance by modulating DD-10 responsiveness. Similarly, using a sequence derived from the 3' terminus, downstream untranslated sequences of regulatory significance can be obtained. The above-mentioned sequences and portions thereof are of use in the identification of cellular factors, such as morphogen-responsive transcriptional activating elements, that participate in the signaling events that lead to DD-10 induction by OP-1 or OP-1 analogs. As described herein, they can be used in reporter gene assays, DNA or RNA footprinting analyses, DNA or RNA gel retardation assays, such as those described below and which require only routine skill to practice.

EXAMPLE 4
Time Course of OP-1 Induced DD-10 Expression

As stated above, morphogens, as defined herein, induce mammalian cells, particularly uncommitted progenitor cells, to include a fully integrated developmental cascade of biological and molecular events that culminate in the morphogenesis of fully differentiated, functional tissue of a type appropriate to the context or local biological environment. The course of expression of individual markers for OP-1 responsiveness is an important aspect of the present invention, as the order of appearance of molecular markers can presumably recapitulate the sequence of events observed, e.g., during chondroblast or osteoblast differentiation, or endochondral bone morphogenesis as induced in vivo by morphogen. Time course analysis of DD-10 expression in morphogen treated C2C12 cells provides a useful in vitro model for the analysis of the morphogen induced cascade of molecular events. Further, substances that function as morphogen analogs and the biological mechanisms associated with such OP-1 activities in tissue morphogenesis can be elucidated.

Figure 8:
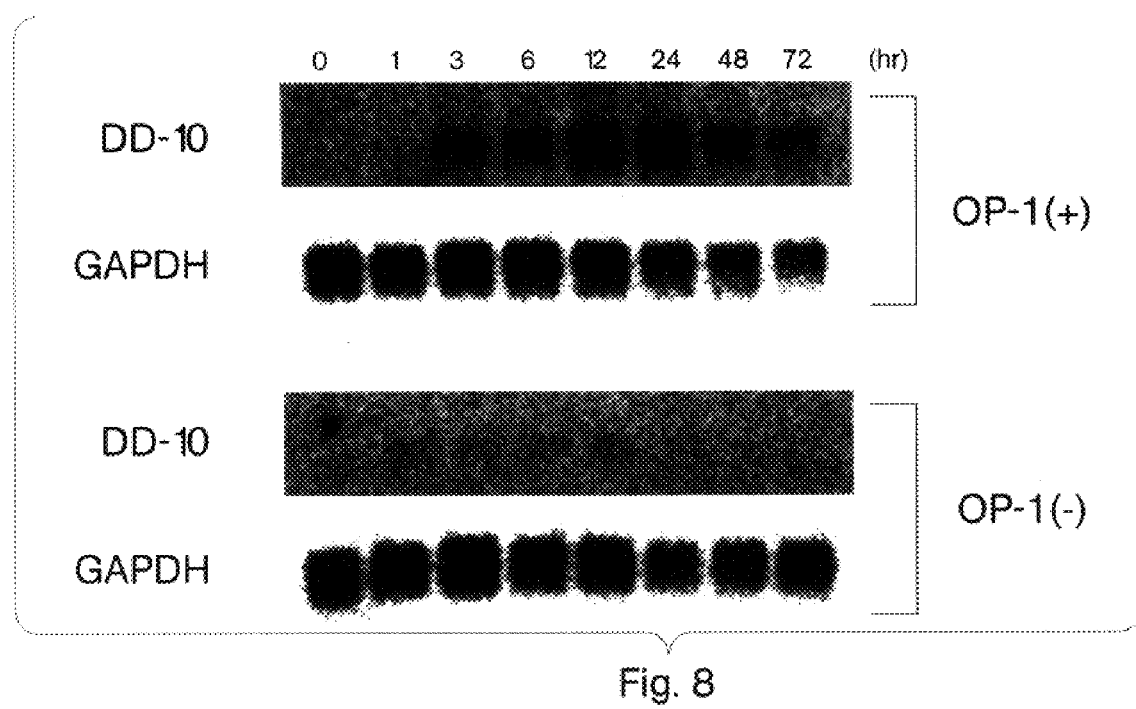
FIG. 8 is a schematic of an autoradiograph of results from an RNA blot analysis demonstrating the time course of DD-10 mRNA induction in C2C12 cells.
Figure 9:
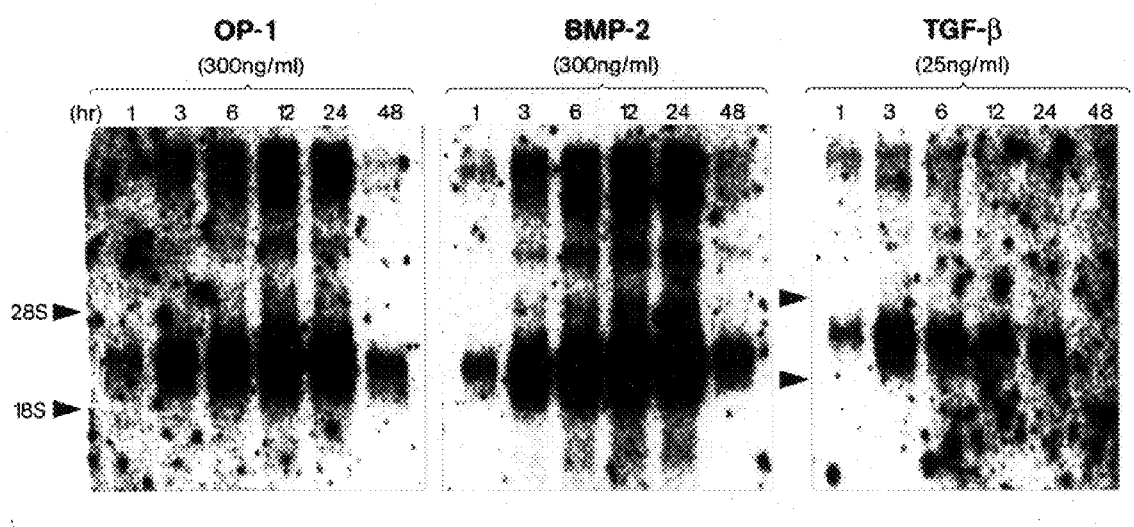
FIG. 9 is a schematic of an autoradiograph of results from an RNA blot analysis demonstrating the induction of DD-10 mRNA by BMP2 and TGF-β in C2C12 cells.

An in vitro time course experiment was used to assess the relative appearance and disappearance of steady-state mRNA levels over a period of 72 h. The experiment revealed that treatment of C2C12 cells with 300 ng/ml OP-1 caused an increase in the levels of a 3 Kb mRNA (corresponding to the DD-10 transcript) which appeared at least as early as 2 h post-treatment, and peaked at least as early as 12–24 h post-treatment, and decreased at approximately 48 h (FIG. 8 top). By contrast, a weak induction of DD-10 mRNA levels several orders of magnitude less was observed 3–12 h after reduction of serum concentration, in the absence of OP-1 (FIG. 8, bottom). In addition, the effect of two other morphogens BMP-2 and TGF-β1, on DD-10 expression was measured. BMP-2 induced DD-10 expression in C2C12 cells to similar levels; however, TGF-β had a significantly less inductive effect compared to that of OP-1 and BMP-2. In addition, the DD-10 cDNA hybridized to several transcripts with varying sizes (4, 5, 7.0 and 9.0 Kb) in response to OP-1 and BMP-2 (FIG. 9). This result suggests the existence of additional DD-10 RNA intermediates or genes products that share homology with DD-10 and can represent members of a gene family responsive to OP-1 and BMP-2 in C2C12 myoblast cells. It is anticipated that any one of said family members, including analogs thereof, can be exploited in all the same manners as DD-10.

EXAMPLE 5

DD-10 Protein Expression

A. General Considerations

DD-10 DNA, DD-10 homolog DNA, or a synthetic form thereof, can be inserted, using conventional techniques well described in the art (see, for example, Maniatis (1989) *Molecular Cloning A Laboratory Manual*), into any of a variety of expression vectors and transfected into an appropriate host cell to produce recombinant DD-10 or DD-10 homologs, such as DD-10 polypeptide chains, including both full length and truncated forms thereof. Production of DD-10 proteins is useful for the production of antibodies which can be used as diagnostic or screening tools for detection of morphogens, including OP-1, activities or proteins having OP-1-like activities such as, for example, DD-10 induction as described herein. The DD-10 specific antibodies also can be used to detect DD-10 in screening assays for molecules competent to induce a morphogen-mediated biological effect.

Useful host cells include prokaryotic (e.g., *E. coli* and *B. subtilis*), and eukaryotic (Saccharomyces and insect/baculovirus) cell systems, myeloma cells, and various other mammalian cells. The full length form of the proteins of this invention preferably are expressed in mammalian cells, as disclosed herein. A vector additionally can include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also can be manipulated to remove potentially inhibiting sequences or to minimize unwanted secondary structure formation. The recombinant putative morphogen also can be expressed as a fusion protein. After being translated, the protein can be purified from the cells themselves or recovered from the culture medium. The DNA also can include sequences that aid in expression and/or purification of the recombinant protein. One useful sequence for example, is a hexa-His ($His_6$) sequence, which adds a histidine tail to anchor the protein to an IMAC Cu2+ column.

For example, the DNA can be inserted into a suitable expression vector for transformation into a prokaryotic host such as *E. coli* or *B. subtilis*. The DNA can be expressed directly or can be expressed as part of a fusion protein having a readily cleavable fusion junction. An exemplary protocol for prokaryotic expression using DD-10 DNA is provided below. Recombinant protein is expressed in inclusion bodies and can be purified therefrom using the technology disclosed in U.S. Pat. No. 5,013,653, for example.

The DNA also can be expressed in a suitable mammalian host. Currently preferred hosts include fibroblast 3T3 cells, (e.g., NIH 3T3, from CRL 1658) COS (simian kidney ATCC, CRL-1650) or CHO (Chinese hamster ovary) cells (e.g., CHO-DXB 11, from Lawrence Chasin, Columbia University, N.Y.). An exemplary protocol for mammalian cell expression of DD-10 DNA in 3T3 cells is provided below.

B. DD-10 Expression in *E. coli*

DD-10 DNA is cloned into a standard commercially available expression vector, (e.g., pET 3a vector, Novagen, Inc. Wisconsin, opened at NcoI and BamH1), and transfected into a bacterial cell line (e.g., BL21 DE3 pLys S cells, Novagen, Inc.) and expressed using standard procedures well described in the art. See, for example, Studier et al., (1990) Methods in Enzymology 185:60–89. Proteins then are isolated from inclusion bodies using standard procedures: Cells are grown overnight in the presence of 1 mM IPTG, lysed, and inclusion bodies isolated by centrifugation. Proteins then are resolubilized and passed over a TSK300 gel filtration column (or suitable equivalent thereof) to partially purify the protein. The protein can be further purified, if desired, by gel electrophoresis. This form of the protein is used as antigen material for antibody production as described in Example 6.

C. DD-10 Expression in CHO Cells

To express the DD-10 protein, the DD-10 DNA is subcloned into an insertion site of a suitable, commercially available vector (e.g., pCDM8, Invitrogen, Inc. San Diego), along with suitable promoter/enhancer sequences and 3' termination sequences. A currently preferred promoter/enhancer sequence combination includes the CMV promoter (human cytomegalovirus (MIE) promoter) present, for example, on pCDM8, as well as the mouse mammary tumor virus promoter (MMTV) boosted by the rous sarcoma virus LTR enhancer sequence (e.g., from Clontech, Inc., Palo Alto). Expression also can be further enhanced using transactivating enhancer sequences. The plasmid also preferably contains DHFR as an ampliflable marker, under SV40 early promoter control (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, NY (1989). Briefly, transfected cells are cultured in medium containing 10% fetal calf serum (FCS), and stably transfected high expression cell lines obtained by amplification subcloning and evaluated by standard Western and Northern blot. Southern blots also can be used to assess the state of integrated DD-10 sequences and the extent of their copy number amplification.

The expressed protein then is purified using standard procedures. If a useful anchor sequence has been added to the DNA, such as a $(His)_6$ sequence, a standard affinity column such as $Cu^{2+}$ IMAC column is a preferred methodology. Here, for example, the cell culture media containing the recombinant protein is passed over a $Cu^{2+}$ IMAC column prepared with 25 mM imidazol. The bound protein then is washed with a compatible solution and eluted with EDTA, and the anchor sequence removed by a standard chemical or enzymatic procedure.

EXAMPLE 6

DD-10 Antibody Production

Recombinantly produced DD-10 proteins can be used to obtain antibodies capable of specific binding to the DD-10 molecules and are useful in immunoassays, as described below, and in the immunopurification of DD-10 and DD-10 like molecules. Antibodies capable of specifically binding DD-10 in vivo can be used in immunohistochemical applications whereby DD-10 can be localized in tissue sections and sections of intact embyros. Coupling DD-10 antibodies, or portions thereof, to immunohistochemical agents requires only routine skill; use of such coupled antibodies is in accordance with any number of well-known techniques for immunohistochemical localization.

For polyclonal antibodies, each rabbit is given a primary immunization (e.g., 500 mg) of recombinantly-produced DD-10 protein or protein fragment specific for DD-10 in 0.1% SDS mixed with 500 ml Complete Freund's Adjuvant. The antigen is injected intradermally at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against DD-10 is detected in the serum using a standard Western blot. Then, the rabbit is boosted monthly with 100 mg/ml of antigen and bled (15 ml per bleed) at days seven and ten after boosting.

Antiserum to DD-10 is obtained using recombinantly produced DD-10 as antigen and the polyclonal antibody production protocol described above. Antiserum reacts specifically with both the *E. coli*-produced and CHO-produced DD-10 proteins as determined by Western blot.

Similarly, monoclonal antibody specific for a given morphogen molecule of interest can be prepared as described below for DD-10. For example, a mouse is given two injections of DD-10 protein or a protein fragment specific for DD-10. The protein preferably is recombinantly produced. The first injection contains 100 mg of DD-10 in complete Freund's adjuvant and is given subcutaneously. The second injection contains 50 mg of DD-10 in incomplete adjuvant and is given intraperitoneally. The mouse then receives a total of 230 mg of DD-10 in four intraperitoneal injections at various times over an eight month period. One week prior to fusion, the mouse is boosted intraperitoneally with DD-10 (e.g., 100 mg) and can be additionally boosted with a DD-10-specific peptide conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for DD-10-specific antibodies using DD-10 as antigen. The cell fusion and monoclonal screening steps readily are performed according to standard procedures well described in standard texts widely available in the art. (See, for example, *Guide to Protein Purification* Murray P. Deutscher, ed., Academic Press, San Diego, 1990.)

EXAMPLE 7

Determining the Tissue Distribution of DD-10

Identification of DD-10 mRNA and proteins provides us with useful reagents for detecting DD-10 in situ, in solutions, and in body fluids using standard methodologies and minor modifications thereof in tissues, fluids and solutions where expression is low. For example, the distribution of DD-10 transcripts can be determined using standard Northern hybridization or in situ hybridization protocols and DD-10 transcript-specific probes or by PCR using DD-10 specific printers. Protein synthesis and distribution is determined using standard Western blot analysis or other immunodetection techniques, e.g., sandwich immunoassays, and antibodies specific to DD-10. Any probe capable of hybridizing specifically to the gene transcript or its protein product, and distinguishing the transcript or protein of interest from other related transcripts can be used. Our ability to detect and monitor DD-10 biosynthesis in tissues, organs, embryos, cultured cells, body fluids, and culture fluids establishes DD-10 as a useful marker protein for OP-1 activity and signal transduction.

Using DD-10-specific nucleotide probes, which can be synthetically engineered or obtained from cloned sequences, DD-10 transcripts can be identified in various tissues, or cell lines of various organisms, using standard methodologies well known to those having ordinary skill in the art. For example, total RNA is prepared from various tissues (e.g., murine embryo and developing and adult liver, kidney, testis, heart, brain, thymus, stomach) by a standard methodologies such as by the method of Chomczynski et al. ((1987) *Anal Biochem* 162:156–159) and described below. Alternatively, RNA can be prepared from cultured cell lines of interest by a similar method. Poly (A)+ RNA is prepared by using oligo (dT)-cellulose chromatography (e.g., Type 7, from Pharmacia LKB Biotechnology, Inc.). Poly (A)+ RNA (generally 15 $\mu$g) from each tissue is fractionated on a 1% agarose/formaldehyde gel and transferred onto a nylon membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating.

Figure 10:
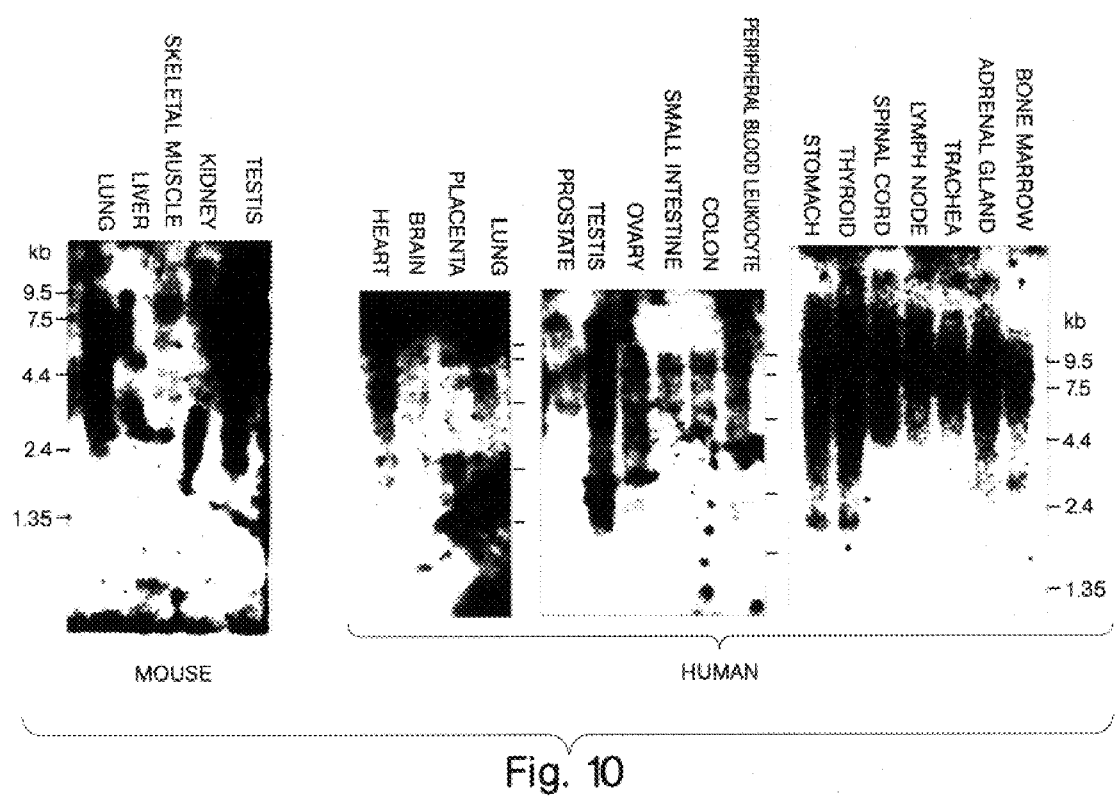
FIG. 10 is a schematic of an autoradiograph of results from an RNA blot analysis demonstrating the tissue distribution of DD-10 transcripts in mice and humans.

For example, a Northern membrane containing 10 g each of total RNA derived from lung, liver, skeletal muscle, kidney and tests of the mouse, as well as human RNA for heart, brain, placenta, lung, prostate, testis, ovary, small intestine, colon, and peripheral blood leukocytes was hybridized with the radio-labeled DD-10 cDNA as described above. DD-10 mRNA was expressed at high levels in the lung and testis in the mouse (FIG. 10). DD-10 mRNA was expressed in most human tissues, at low levels. The differential tissue distribution of DD-10 mRNA suggests that its expression is under tissue specific control. The hybridization of the mouse DD-10 probe with human mRNAs suggests that there is an analog or homolog of DD-10 mRNA in humans. Furthermore, the differential, apparently ubiquitous, expression compared to that in mice suggests that the factors that regulate tissue specificity in mice are not present, or are different, in humans.

A detailed description of a suitable hybridization protocol is described in Ozkaynak, et al., (1991) *Biochem. Biophys. Res. Commn.* 179:116–123, and Ozkaynak, et al. (1992) *J Biol. Cm.*26:25220–25227.

EXAMPLE 8
Screening Assays for OP-1 Like Compounds (Morphogen Mimetics) Which Induce and/or Alter DD-10 Levels Further to the identification and quantification of DD-10 mRNA and protein production candidate morphogen analogs can be evaluated for their ability to mimic morphogens or to inhibit morphogens (e.g., morphogen agonists or antagonists) by monitoring the effect of the analogs on an appropriate morphogen responsive cell line. Morphogen agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. Morphogen antagonists are envisioned to have utility in applications where tissue morphogenesis is to be limited as, for example, in the treatment of malignant transformations including, but not limited to, osteosarcomas, Paget's disease, and fibrodysplasia ossificans progressiva (See, for example, Roush (1996) *Science* 273:1170).

Candidate compounds which can be administered to modulate the level of DD-10 can be found using the following screening assay, in which the level of DD-10 protein or RNA production by a cell which produces measurable levels of DD-10 is determined by incubating the cells in the presence and absence of the candidate compound. The protocols are based on procedures for identifying compounds which alter endogenous levels of morphogen expression, a detailed description also can be found in PCT US 92/07359, incorporated herein by reference.

Cell cultures of kidney, adrenals, urinary bladder, brain, or other organs, can be prepared as described widely in the literature. For example, kidneys can be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues can be established in multiwell plates (6 well or 24 well) according to conventional cell culture techniques, and are cultured in the absence or presence of serum for a period of time (1–7 days). Cells can be cultured, for example, in DMEM containing 10% fetal calf serum or in serum-deprived medium or in defined medium (e.g., containing insulin, transferring, glucose, albumin, or other growth factors). Test compounds are added to the cultured cells and DD-10 biosynthesis monitored and measured at various time points using the methods described previously herein. As described in Example 7, the cells and their culture fluids are assayed either for mRNA levels, using Northern blot analysis and DD-10 mRNA specific probes, or for protein levels, using DD-10 specific antibodies. For example, DD-10 protein can be measured on a tissue section or cell directly using standard immunofluorescence techniques or in culture fluids and body fluids using a sandwich immunoassay.

To ascertain the particular time point at which DD-10 is produced following treatment with a candidate morphogen, cells treated with the candidate morphogen are collected periodically and evaluated for DD-10 production, as described above. To monitor de novo DD-10 synthesis, some cultures are labeled according to conventional procedures with an 35S-methionine/35S-cysteine mixture for 6–24 hours and then evaluated to quantitate DD-10 synthesis by conventional immunoassay methods. Alternatively, anti-DD-10 antibodies can be labeled and incubated with the cells or cell lysates, and the bound complexes detected and quantitated by conventional means, such as those described hereinabove. Tissues can also be examined directly for the synthesis of DD-10 mRNA using the art-recognized technique of in situ hybridization.

The ability to detect DD-10 protein in solution provides a valuable tool for diagnostic assays, allowing us to monitor the levels of DD-10 free in the body, e.g., in serum, urine, spinal or peritoneal fluid, breast exudate, and other body fluids in order to assess the presence of OP-1 or OP-1 analog activity. The present invention therefor provides a means of identifying naturally occurring or synthetic proteins or other factors or drugs that have OP-1-like activities.

OP-1 is an intimate participant in normal bone growth and resorbtion. Thus, soluble OP-1 is expected to be detected at higher concentrations in individuals experiencing high bone formation, such as children, and at substantially lower levels in individuals with abnormally low rates of bone formation, such as patients with osteoporosis, aplastic bone disease, or osteopenia. Monitoring the level of OP-1 in serum thus provides a means for evaluating the status of bone tissue and bone homeostasis in an individual, as well as a means for monitoring the efficacy of a treatment to regenerate damaged or lost bone tissue.

For serum assays, for example, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble morphogen complex or mature morphogens relative to that of the other proteins present in serum. Further purification also can be achieved by chromatographic techniques well known in the art. The sample fluid then can be assayed for morphogens using the morphogen specific antibodies and sandwich assays as described herein.

The present invention therefor also provides a test cell or cell line which expresses an exogenously introduced DD-10 protein, which is responsive to OP-1. Said cell or cell line can be also used as described herein, to replace cell lines that produce DD-10 endogenously, for the screening assays described herein above.

Alternatively, a test cell comprising a reporter gene construct containing an OP-1 responsive DD-10 promoter or an OP-1 responsive transcriptional activating element within the DD-10 upstream sequences described above, can be used to determine the ability of candidate morphogens or their analogs to induce signal transduction across a cell membrane following receptor binding. The assay provides a readout of a chemiluminescent marker protein that is used for the rapid assessment of OP-1-like behavior of test samples. Further, it can be used in the analysis of the transcription factors involved in OP-1 regulated transcription or that of other morphogens or morphogen analogs.

The DD-10 genomic DNA is used to prepare a series of deletion constructs carrying the luciferase reporter gene and portions of the DD-10 gene promoter. A promoterless pGL2-basic plasmid comprising a nucleotide sequence encoding the detectable enzyme luciferase (Promega, Madison Wis.) is employed as the basic vector. An intact DD-10 promoter sequence (corresponding to any one of nucleotides 1-904, 121-780 or 600–900 of SEQ. ID No. 1) is inserted into the pGL2 plasmid following digestion with KpnI and MluI. Similarly, serial 5' deletion fragments (e.g., prepared by PCR methods as described above) are subcloned into KpnI and MluI digested preparations of the pGL2 plasmid. Thus, the cloned promoter DNA or a portion thereof is placed in transcriptionally operative association with the luciferase reporter gene.

The vectors are transfected into C2C12 myoblast cells or other desired cell line using standard techniques. Briefly, cells are plated in 12-well culture dishes ($1\times10^5$ cell/well) in DMEM containing 15% fetal bovine serum. Seventy-two hours later, the above-described vectors are transfected into the cultured cells, using, e.g., a calcium phosphate method, in complete medium for 6 hours. A 10% solution DMSO in PBS is used to terminate transfection. Thereafter, transfected cells are cultured in complete media. Twenty-four hours later, transfected cells are contacted with OP-1 or test compound and further cultured for an additional 24 hours. Luciferase activity induced by the exogenously added morphogen candidate is measured using the Promega Luciferase Assay System (Promega, Madison Wis.) and a luminometer (Turner Designs, Promega).

Further, tissues can be examined directly for the synthesis of DD-10 mRNAs using the art-recognized technique of in situ hybridization.

DD-10 therefor comprises a useful marker protein for the detection of morphogen activity, such as OP-1 activity. For example, the present invention provides a means of monitoring the level of OP-1 activity, or the like, in experimental animals or patients undergoing treatment with OP-1 or OP-1 analogs. That is, test substances can be injected into appropriate sites within a mouse or Xenopus embryo or into a damaged adult organ and DD-10 mRNA or protein levels monitored to detect morphogenic activity. Further, the present invention provides a method for detecting the activity of morphogen analogs and any other factor that can induce OP-1 signaling (e.g., a morphogen that can mimic OP-1 or can induce OP-1 biosynthesis).

EXAMPLE 9
Additional Morphogen Analog Assays

Confirmation of the OP-1-like activities apparently possessed by candidate morphogens as identified by their ability to induce DD-10 synthesis can be achieved by testing for their ability to induce differentiation of primary osteoblasts, by measuring the ability of the potential analog to induce production of alkaline phosphatase, PTH-mediated cAMP and osteocalcin, all of which are induced when primary osteoblasts are exposed to OP-1, 60A or DPP.

In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast cultures obtained from established cell lines. (Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.)

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) *PNAS* 72:3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that the cells are in serum-deprived growth medium at the time of the experiment.

A. Alkaline Phosphatase Induction in Osteoblasts

The cultured cells in serum-free medium are incubated with morphogen (e.g., OP-1), morphogen analog or a negative control, using a range of concentrations. For example, 0.1, 1.0, 10.0, 40.0 or 80.0 ng OP-1/ml medium typically are used. 72 hours after the incubation period the cell layer is extracted with 0.5 ml of 1% Triton X-100. The resultant cell extract then, is centrifuged, and 100 ml of the extract is added to 90 ml of paranitrosophenylphospate (PNPP)/glycerine mixture and incubated for 30 minutes in a 37° C. water bath and the reaction stopped with 100 ml NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the Biorad method. Alkaline phosphatase activity is calculated in units/mg protein, where 1 unit=1 nmol p-nitrophenol liberated/30 minutes at 37° C. OP-1 induces a five-fold increase in the specific activity of alkaline phosphate by this method. Agonists are expected to have similar induction effects. Antagonists should inhibit or otherwise interfere with morphogen binding, and diminished alkaline phophatase induction should result when the assay is performed with an antagonist in the presence of a limiting amount of morphogen.

B. Induction of PTH-Mediated cAMP

The effect of a morphogen analog on parathyroid hormone-mediated cAMP production in rat osteoblasts in vitro can be demonstrated as follows. Rat osteoblasts are prepared and cultured in a multiwell plate as described above. The cultured cells then are divided into three groups: (1) wells which receive, for example, 1.0, 10.0 and 40.0 ng OP-1/ml medium; (2) wells which receive the candidate analog at various concentration ranges; and (3) a control group which receives no additional factors. The plate is then incubated for another 72 hours. At the end of the 72 hours the cells are treated with medium containing 0.5% bovine serum albumin (B SA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). OP-1 doubles cAMP production in the presence of PTH. Agonists are expected to have similar induction effects. Antagonists are expected to inhibit or otherwise interfere with morphogen binding, and diminished cAMP production should result when the assay is performed with an antagonist in the presence of limiting the amount of morphogen.

C. Induction of Osteocalcin Production

Osteocalcin is a bone-specific protein synthesized by osteoblasts which plays an integral role in determining the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate morphogenic efficacy in vitro.

Rat osteoblasts are prepared and cultured in a multi-well plate as described above. In this experiment the medium is supplemented with 10% FBS, and on day 2, cells are fed with fresh medium supplemented with fresh 10 mM b-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. Morphogen or morphogen analog then is added to the wells directly, e.g., in 50% acetonitrile (or 50% ethanol) containing 0.1% trifluoroacetic acid (TFA), at no more than 5 ml morphogen/ml medium. Control wells receive solvent vehicle only. The cells then are re-fed and the conditioned medium sample diluted 1:1 in standard radio-immunoassay buffer containing standard protease inhibitors and stored at −20° C. until assayed for osteocalcin. Osteocalcin synthesis is measured by standard radioimmunoassay using a commercially available osteocalcin-specific antibody and can be confirmed by Northern blot analysis to calculate the amount of osteocalcin mRNA produced in the presence and absence of OP-1 or morphogen analog. OP-1 induces a dose-dependent increase in osteocalcin production (5-fold increase using 25 ng of OP-1 protein/ml), and a 20-fold increase in osteocalcin mRNA. Agonists are expected to have similar induction effects; antagonists are expected to inhibit or otherwise interfere with morphogen binding, thereby substantially interfering with osteocalcin induction in the presence of a limiting amount of morphogen.

Mineralization is determined on long term cultures (13 day) using a modified von Kossa staining technique on fixed cell layers: cells are fixed in fresh 4% paraformaldehyde at 23° C. for 10 min, following rinsing with cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture. OP-1 induces a 20-fold increase in initial mineralization rate. Agonists are expected to have similar induction effects; antagonists are expected to inhibit or otherwise interfere with morphogen binding, thereby inhibiting mineralization induction in the presence of a limiting amount of morphogen.

D. Inhibition of Epithelial Cell Growth by OP-1

OP-1 is known to inhibit epithelial cells. Thus, the ability of a candidate analog to inhibit cell proliferation, as measured by $^3$H-thymidine uptake by an epithelial cell can be used in an assay to evaluate signal transduction activity of the candidate. Analogs competent to inhibit epithelial cell growth are contemplated to have particular utility in therapeutic applications where limitation of a proliferating cell population is desired. Such applications include chemo-therapies and radiation therapies where limiting the growth of a normally proliferating population of cells can protect these cells from the cytotoxic effects of these cancer therapies. (see e.g., WO 94/06420). In addition, psoriasis and other tissue disorders resulting from uncontrolled cell proliferation, including benign and malignant neoplasis, can be modulated by use of an OP-1 analog.

As an example, mink lung epithelial cell growth is inhibited by OP-1. (see, PCT US93/08885; WO 94/06420.) As described above, derivatives of these cells (e.g., "R-4 mutants", clone 4-2, Laiho et al. (1990) J. Biol. Chem. 265: 18518–18524) can be transfected with DNA encoding OP-1-specific receptors and induced to express these receptors. The transfected cells, then can be assayed for a candidate analog's ability to block cell growth. As one example, when R-4 cells are transfected with ALK-1 under a $Zn^{2+}$-inducible promoter, and induced to express the receptor following induction with $ZnCl_2$, cell growth can be inhibited in the presence of OP-1 in a dose dependent manner.

In a typical assay, cells are seeded in 24-well cell culture plates at a density of 104 cells per well in DMEM with 10% FBS, and incubated overnight. The medium is replaced with DMEM containing 0.2% FBS and 100 $\mu$M $ZnCl_2$, and the cells are incubated for 5 h, after which the medium is replaced with fresh DMEM containing 0.2% FBS, 100 $\mu$M $ZnCl_2$ and various concentrations of OP-1 or an analog candidate. After 16 h of incubation, 0.25 Ci of $^3$H-thymidine (Amersham) are added and the cells incubated for an additional 2 h. Thereafter, the cells are fixed in 10% trichloro-acetic acid for more than 15 min on ice, and solubilized with 1 M NaOH. The cell extracts are neutralized with 1 M HCl and $^3$H radioactivity determined in a liquid scintillation counter.

EXAMPLE 10

General Morphogen Analog Formulation/Administration Considerations

The morphogen analogs, morphogen inducers, therapeutics, agonists of morphogen receptors and/or intracellular inducers of the present invention can be administered by any route which is compatible with the particular morphogen, inducer, or agonist employed. Thus, as appropriate, administration can be oral or parenteral, including intravenous and intraperitoneal routes of administration. In addition, administration can be by periodic injections of a bolus of the morphogen, inducer or agonist, or can be made more continuous by intravenous or intraperitoneal administration from a reservoir which is external (e.g., an i.v. bag) or internal (e.g., a bioerodable implant). In certain embodiments, the compositions of the instant invention can be therapeutic-grade. That is, certain embodiments comply with standards of purity and quality control required for administration to humans. Veterinary applications are also within the intended meaning as used herein.

Useful solutions for oral or parenteral administration can be prepared by any of the methods well known in the pharmaceutical art, described, for example, in *Remington's Pharmaceutical Sciences,* (Gennaro, A., ed.), Mack Pub., 1990. Formulations can include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, can be useful excipients to control the release of the morphogen in vivo.

Other potentially useful parenteral delivery systems for these morphogen analogs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally.

Formulations for parenteral administration can also include glycocholate for buccal administration, methoxysalicylate for rectal administration, or cutric acid for vaginal administration. Suppositories for rectal administration also can be prepared by mixing the morphogen, inducer or agonist with a non-irritating excipient such as cocoa butter or other compositions which are solid at room temperature and liquid at body temperatures.

Formulations for topical administration to the skin surface can be prepared by dispersing the morphogen, inducer or agonist with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

Alternatively, the agents described herein can be administered orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590). In addition, at least one morphogen, OP-1, has been identified in mammary gland extract, colostrum and 57-day milk. Moreover, the OP-1 purified from mammary gland extract is morphogenically active and also is detected in the bloodstream. Finally, soluble form morphogen, e.g., mature morphogen associated with the pro domain, is morphogenically active. These findings, as well as those disclosed in the examples below, indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also can be associated with molecules capable of enhancing their solubility in vitro or in vivo.

As will be appreciated by the artisan skilled in the art, where the analog to be provided as a therapeutic is amino-acid based, the nucleic acid encoding the polypeptide also can be provided to a cell of interest by cellular absorption for endogenous expression. Such methods are well known and well described in the art. See, for example W095/2261 1, published Aug. 24, 1995, and Example 13, herein below.

The compounds provided herein also can be associated with molecules capable of targeting the morphogen, inducer or agonist to the desired tissue. For example, an antibody, antibody fragment, or other binding protein that interacts specifically with a surface molecule on cells of the desired tissue, can be used. Useful targeting molecules can be designed, for example, using the single chain binding site technology disclosed, for example, in U.S. Pat. No. 5,091,513.

The morphogen analogs also can be associated with means for targeting the analog to a desired tissue. For example, tetracycline and diphosphonates (bisphosphonates) are known to bind to bone mineral, particularly at zones of bone remodeling, when they are provided systemically in a mammal. Accordingly, these molecules can be included as useful agents for targeting analogs to bone tissue. Alternatively, an antibody or other binding protein that interacts specifically with a surface molecule on the desired target tissue cells also can be used. Such targeting molecules further can be covalently associated to the morphogen analog e.g., by chemical crosslinking, or by using standard genetic engineering means to create, for example, an acid labile bond such as an Asp-Pro linkage. Useful targeting molecules can be designed, for example, using the single chain binding site technology disclosed, for example, in U.S. Pat. No. 5,091,513.

Finally, morphogen analogs can be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents and analgesics and anesthetics.

Morphogen analogs further can be formulated into pharmaceutical compositions by admixture with pharmaceutically acceptable nontoxic excipients and carriers. As noted above, such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition can include the morphogen dispersed in a fibrinogen-thrombin composition or other bioadhesive such as is disclosed, for example in PCT US91/09275, the disclosure of which is incorporated herein by reference. The composition then can be painted, sprayed or otherwise applied to the desired tissue surface. Alternatively, the compositions can be formulated for parenteral or oral administration to humans or other mammals in therapeutically effective amounts, e.g., amounts which provide appropriate concentrations of the analog to target tissue for a time sufficient to induce the desired effect.

Where the analog is to be used as part of a transplant procedure, it can be provided to the living tissue or organ to be transplanted prior to removal of tissue or organ from the donor. The analog can be provided to the donor host directly, as by injection of a formulation comprising the analog into the tissue, or indirectly, e.g., by oral or parenteral administration, using any of the means described above.

Alternatively or, in addition, once removed from the donor, the organ or living tissue can be placed in a preservation solution containing the morphogen analog. In addition, the recipient also preferably is provided with the analog just prior to, or concomitant with, transplantation. In all cases, the analog can be administered directly to the tissue at risk, as by injection to the tissue, or it can be provided systemically, either by oral or parenteral administration, using any of the methods and formulations described herein and/or known in the art.

Where the morphogen analog comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell (solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also can contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components can be found, for example, in U.S. Pat. No. 5,002,965, the disclosure of which is incorporated herein by reference.

As will be appreciated by one of ordinary skill in the art, the formulated compositions contain therapeutically effective amounts of the morphogen, morphogen inducers or agonists of morphogen receptors. That is, they contain amounts which provide appropriate concentrations of the agent for a time sufficient to stimulate morphogenesis.

The concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the morphogen analogs of this invention can be provided to and individual where typical dose ranges are from about 10 ng/kg to about 1 g/kg of body weight per day; a preferred dose range being from about 0.1 mg/kg to 100 mg/kg of body weight. No obvious morphogen-induced pathological lesions are induced when mature morphogen (e.g., OP-1, 20 mg) is administered daily to normal growing rats for 21 consecutive days. Moreover, 10 mg systemic injections of morphogen (e.g., OP-1) injected daily for 10 days into normal newborn mice does not produce any gross abnormalities.

Finally, as noted above, in another series of embodiments, cells can be utilized to serve as a source of morphogen or agonist. These cells can be progenitor cells, or progenitor cells which have been induced to undergo differentiation. The cells can be derived from a donor (e.g., a tissue-type matched donor, sibling, identical twin), can be derived from a tissue culture (e.g., undifferentiated or partly undifferentiated cells in culture; fetal tissue culture), or can be explanted from the subject and then be re-implanted after proliferation and/or differentiation. Preferably, the cells are induced to undergo differentiation by treatment with a morphogen (e.g., OP-1) either before or after implantation. Thus, for example, progenitor cells can be explanted from a subject, allowed or caused to proliferate in vitro, be induced to undergo differentiation by morphogen treatment, and be re-implanted where they can provide a source of morphogen or agonist.

EXAMPLE 11
DD-10 Mediates A Developmental Response In Xenopus

Figure 12:
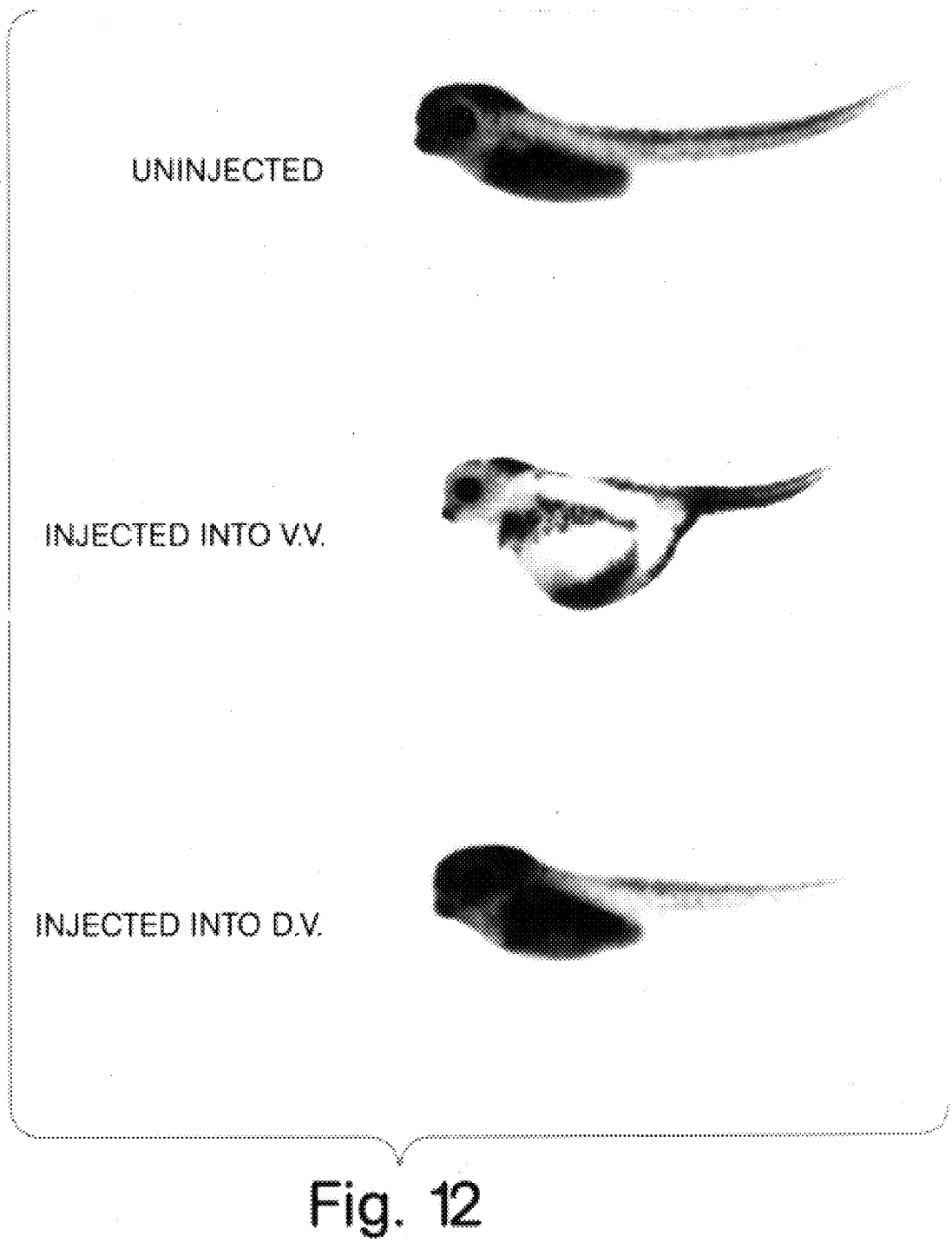
FIG. 12 shows secondary axis formation in Xenopus embryos after injection of DD-10 mRNA.

Morphogens as defined herein are known to mediate aspects of Xenopus morphogenesis such as dorsal-ventral patterning in the early Xenopus embryo. (See, for example, Graff et al. (1994) *Cell* 79:169–179; Suzuki et al. (1994) *Proc. Natl. Acad. Sci.* 9:10255–10259, Schmidt et al. (1995) *Developmental Biology* 169:37–50; and, Mahoney et al. (1995) *Proc. Natl. Acad. Sci.* 92:6474–6478, the disclosure of each of the foregoing are herein incorporated by reference). To illustrate that DD-10, on its own, is competent to induce a morphogen-mediated biological response, the DNA encoding the ORF of DD-10 was in vitro transcribed and injected into various sites in a Xenopus embryo. When 1 ng of DD-10 mRNA was injected into a ventro-vegetal site of 8–16 cell stage embryo, a secondary axis formation was clearly and reproducibly observed (FIGS. 11 and 12). No phenotype was observed when the DD-10 mRNA was injected into a dorso-vegetal site. This experiment was performed three times with similar results. DD-10 is competent to direct cell fate and induce cell differentiation. Accordingly, DD-10 itself can be used as a marker of the progress of cell differentiation and tissue morphogenesis. In addition, DD-10 itself, or an analog thereof, can be used to induce cell differentiation and tissue morphogenesis. As will be understood by the artisan of ordinary skill in the art, the analog can be a species or other naturally derived variant of the gene defined in FIG. 7. Alternatively, it can be a biosynthetic variant thereof. It also can be a DD-10 functional mimetic, which can or can not be structurally related to DD-10. Such a mimetic can be identified using the candidate compound screening methodology described herein, and testing for the presence of a morphogenesis marker that occurs further along the pathway, such as, in the case of osteoblast cells, alkaline phosphatase and/or calcium content (see hereinabove).

As will also be appreciated by the skilled artisan, DD-10 can be provided to a responsive cell as a DD-10 protein. Alternatively, DD-10 DNA can be provided for cell uptake and intracellular expression as described in Example 13.

EXAMPLE 12
DD-10 Anti-Sense DNA and Methods of Use Thereof

The present invention also provides oligonucleotides, including modified versions thereof, which have antisense homology to a sufficient portion of the DD-10 mRNA or gene such that they inhibit the expression of that gene. The inhibition of the expression of the DD-10 gene can cause significant phenotypic effects as described below, which can be assessed by standard techniques used to measure RNA (e.g., Northern blot analysis or RT-PCR) or protein, using DD-10 specific antibodies (e.g., Western blot analysis or immunofluorescence) as described herein.

The term antisense, antisense DNA, or antisense oligonucleotide, as used herein, includes oligonucleotides that are oligodeoxyribonucleotides, oligoribonucleotides, or modified versions thereof, which hybridize to an mRNA of a gene of interest or to the gene itself, thereby inhibiting the translation of that mRNA or the transcription of that gene, respectively. In particular, a DD-10 antisense oligonucleotide is an oligonucleotide that hybridizes to DD-10 mRNAs or DNA, or to modified allelic, or homologous variants thereof and inhibit translation/transcription of that mRNA/gene, respectively.

The antisense molecules are designed so as to selectively interfere with translation or transcription of DD-10 upon hybridization with their target, i.e., to hybridize substantially more to the target sequence than to any other sequences in the target cell.

Based upon the nucleotide sequence depicted in FIG. 6 or in SEQ. ID No. 1, the skilled artisan can easily choose, or design, and synthesize any of a number of appropriate antisense molecules. Such antisense oligonucleotides should comprise a sequence of 10–30 consecutive bases that are complementary to DD-10 mRNA. In preferred embodiments, the antisense oligonucleotides correspond to the complement of N-terminal or 5' upstream sites. Most preferably, the oligonucleotide is designed to hybridize with the translation initiation site or within the 5' untranslated region (UTR). In addition, transcription initiation or promoter sites or 3' UTR can be targeted. Preferably, the antisense oligonucleotide is targeted to sites in which mRNA secondary structure is not expected and to which proteins are not expected to bind. Similarly, antisense to allelic or homologous mRNAs and genomic DNAs are enabled without undue experimentation.

Although it is preferable that the antisense oligonucleotide is perfectly complementary to the DD-10 mRNA or gene, this is not strictly necessary provided the oligonucleotide has sufficient length and complementarity so as to hybridize to DD-10 mRNA. Those skilled in the art will recognize that the exact length of the antisense oligonucleotide and its degree of complementarity will depend upon the specific target sequence selected. It is preferred that the antisense oligonucleotide be selected so as to hybridize selectively with the target under physiological conditions, i.e., to hybridize substantially more with the target sequence than with any other sequence in the target cell under physiological conditions.

Alternatively, the antisense oligonucleotide can be a self-stabilized hairpin or hammerhead ribozyme as described by Cech, T. R. (1988) J. Am. Med. Assoc. 260: 3030–3034. For example, a hammerhead ribozyme contains an internal conserved portion and variable 5' and 3' ends which are designed to bind to an mRNA of interest on either side of a NUX (N=A, U, G or C; X=A, U or C) consensus triplet. The internal portion of the ribozyme antisense oligonucleotide forms a hammerhead $2^0$ structure upon binding to target mRNA due to intramolecular base pairing, and contains a catalytic domain that is capable of cleaving the target mRNA molecule 3' of the NUX triplet. Preferably, the outermost 7 nucleotides at each end of the ribozyme bind complementarily to the target mRNA. It is preferred that the ribozyme is AU rich. The advantage to a ribozyme approach for inhibiting gene expression is that ribozyme molecules catalytically cleave their target RNA and are capable of cleaving more than one mRNA molecule, thus, in theory, requiring less ribozyme/cell to effect complete blockage of protein synthesis.

As contemplated herein, the DD-10-antisense oligonucleotides can be composed of deoxyribonucleotides, ribonucleotides, or any combination thereof. The 5' end of one nucleotide and the 3' end of another nucleotide can be covalently linked, as in natural systems, via a phosphodiester internucleotide linkage. These oligonucleotides can be prepared by art recognized methods such as phosphoramidate, H-phosphonate chemistry, or methylphosphoramidate chemistry (see, e.g., Uhlmann et al. (1990) Chem. Rev. 90:543–584; Agrawal (ed.) Meth, Mol., Biol.Humana Press, Totowa, N.J. (1993) Vol. 20; and U.S. Pat. No. 5,149,798) which can be carried out manually or by an automated synthesizer (reviewed in Agrawal et al. (1992) Trends Biotechnol. 10:152–158).

The DD-10-antisense oligonucleotides also can include modified oligonucleotides. That is, the oligonucleotides can be modified in a number of ways which do not compromise their ability to hybridize to nucleotide sequences contained within, e.g., the transcription initiation region or coding region of the DD-10 gene. The term modified oligonucleotide as used herein describes an oligonucleotide in which at least two of its nucleotides are covalently linked via a synthetic linkage, i.e., a linkage other than a phosphodiester linkage between the 5' end of one nucleotide and the 3' end of another nucleotide. The most preferred synthetic linkages are phosphorothioate linkages. Additional preferred synthetic linkages include alkylphosphonates, phosphorodithioates, phosphate esters, alkylphosphonothioates, phosphoramidates, carbamates, carbonates, phosphate triesters, acetamidate, and carboxymethyl esters. Oligonucleotides with these linkages or other modifications can be prepared according to known methods (see, e.g., Agrawal and Goodchild (1987) Tetrahedron Lett. 28:3539–3542; Agrawal et al. (1988) Proc. Natl. Acad. Sci. (USA) 85:7079–7083; Uhlmann et al. (1990) Chem. Rev. 90:534–583; Agrawal et al. (1992) Trends Biotechnol. 10:152–158; Agrawal (ed.) Meth. Mol. Biol., Humana Press, Totowa, N.J. (1993) Vol. 20).

The term modified oligonucleotide also encompasses oligonucleotides with a modified base and/or sugar. For example, modified oligonucleotides include oligonucleotides having the sugars at the most 3' and/or most 5' positions attached to chemical groups other than a hydroxyl group at the 3' position and other than a phosphate group at the 5' position. Other modified ribonucleotide-containing oligonucleotides can include a 2'-O-alkylated ribose group such as a 2'-O-methylated ribose, or oligonucleotides with arabinose instead of ribose. In addition, unoxidized or partially oxidized oligonucleotides having a substitution in one nonbridging oxygen per nucleotide in the molecule are also considered to be modified oligonucleotides.

Such modifications can be at some or all of the internucleoside linkages, at either or both ends of the oligonucleotide, and/or in the interior of the molecule (reviewed in Agrawal et al. (1992) Trends Biotechnol. 10:152–158 and Agrawal (ed.) Meth. Mol. Biol., Humana Press, Totowa, N.J. (1993) Vol. 20). Also considered as modified oligonucleotides are oligonucleotides having nuclease resistance-conferring bulky substituents at their 3' and/or 5' end(s) and/or various other structural modifications not found in vivo without human intervention. Other modifications include additions to the internucleoside phosphate linkages, such as cholesteryl or diamine compounds with varying numbers of carbon residues between the amino groups and terminal ribose.

DD-10-antisense oligonucleotides or other DD-10 inhibitors can be administered as part of a pharmaceutical composition to an experimental organism such as, but not limited to, mouse. Such a pharmaceutical composition can include the DD-10 inhibitor in combination with any standard physiologically and/or pharmaceutically acceptable carriers which are known in the art. The characteristics of the carrier will depend on the route of administration. Physiologically and pharmaceutically acceptable carriers include diluents, fillers, salts, buffers, stabilizers, solubilizers, and other materials which are well known in the art.

The pharmaceutical composition of the invention can also contain other active factors and/or agents which inhibit DD-10 expression or otherwise inhibit morphogenesis. Such additional factors and/or agents can be included in the pharmaceutical composition to produce a synergistic effect or to minimize side-effects caused by the DD-10 inhibitor of the invention.

The pharmaceutical composition of the invention can be in the form of a liposome in which DD-10-antisense oligonucleotides are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, the disclosures of which are herein incorporated by reference.

The pharmaceutical composition of the invention can further include compounds such as cyclodextrins and the like which enhance delivery of oligonucleotides into cells, as described in the art. When the composition is not administered systemically but, rather, is injected at the site of the target cells, cationic detergents (e.g. Lipofectin) can be added to enhance uptake.

When a therapeutically effective amount of a DD-10 inhibitor is administered orally, the inhibitor will be in the form of a tablet, capsule, powder, solution or elixir. When administered in tablet form, the pharmaceutical composition of the invention can additionally contain a solid carrier such as a gelatin or an adjuvant. The tablet, capsule, and powder can contain preferably from about 25 to 90% of the DD-10 oligonucleotide. When administered in liquid form, a liquid carrier such as water, petroleum, oils of animal or plant origin such as peanut oil, mineral oil, soybean oil, sesame oil, or synthetic oils can be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition can contain from about 0.5 to 90% by weight of a DD-10-antisense oligonucleotide and preferably from about 1 to 50% of the oligonucleotide.

The inhibition of DD-10 expression need not be accomplished by means of a DD-10 antisense oligonucleotide. Rather, inhibitors of DD-10 transcription or DD-10 protein activity also can be employed to the same effect. For example, antibodies or fragments of antibodies which act intracellularly against the DD-10 protein.

In another series of embodiments, a recombinant gene is constructed which encodes a DD-10 antisense oligonucleotide and this gene is introduced within the targeted cells on a vector. Such a DD-10-antisense gene can, for example, consist of the normal DD-10 sequence, or a subset of the normal DD-10 sequence, operably joined in reverse orientation to a promoter region. An operable DD-10-antisense gene can be introduced on an integration vector or can be introduced on an expression vector. In order to be most effective, it is preferred that the DD-10 antisense sequences be operably joined to a strong eukaryotic promoter which is inducible or constitutively expressed.

When a therapeutically effective amount of a DD-10 inhibitor is administered by intravenous, cutaneous or subcutaneous injection, the inhibitor will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the DD-10 inhibitor, an isotonic vehicle such as Sodium Chloride Injection, Ringer's Injection, Dextrose Injection, Dextrose and Sodium Chloride Injection, Lactated Ringer's Injection, or another vehicle as known in the art. The pharmaceutical composition of the present invention can also contain stabilizers, preservatives, buffers, antioxidants, or other additives known to those of skill in the art.

In preferred embodiments, when the target cells are readily accessible, administration of DD-10-antisense oligonucleotides is localized to the region of the targeted cells in order to maximize the delivery of the DD-10-antisense, minimize DD-10 inhibition in non-target cells, and minimize the amount of DD-10-antisense needed per treatment. Thus, in one preferred embodiment, administration is by direct injection at or perfusion of the site of the targeted cells, such as a tumor. Alternatively, the DD-10-antisense oligonucleotides can be adhered to small particles, such as microscopic gold beads which are impelled through the membranes of the target cells (see, e.g., U.S. Pat. No. 5,149,655, the disclosure of which is herein incorporated by reference). Alternatively still, the antisense oligonucleotides can be administered in association with a suitable "matrix," as described herein in Example 13.

In all of the above-described methods of treatment, the DD-10 inhibitors are administered in therapeutically effective amounts. In addition, in those methods in which the experimental animal or patient also is subjected to treatment that induces a DD-10-dependent pathway, these treatments are also administered in therapeutically effective amounts. As used herein, the term "therapeutically effective amount" means the total amount of each active component of the pharmaceutical composition or method that is sufficient to show a meaningful patient benefit, i.e., the killing or inhibition of the growth of the target cells. When applied to an individual active ingredient, administered alone, the term refers to that ingredient alone. When applied to a combination, the term refers to combined amounts of the active ingredients that result in the therapeutic effect, whether administered in combination, serially or simultaneously.

In order to investigate the importance of DD-10 or other proteins such as morphogens, antisense oligonucleotide technology can be used to inhibit the expression of a chosen gene. The specificity of antisense technology affords the ability to analyze the consequences of such inhibition in cell lines such as but not limited to, by monitoring variations in their differentiation pattern or their biosynthetic profile, or in the whole organism; by monitoring morphogenesis in Xenopus embryos. In particular, antisense oligonucleotides that bind to DD-10 mRNA inhibit its translation and therefor can inhibit the ability of OP-1 to induce chondroblast or osteoblast phenotypes or other downstream developmental events. In addition, the inhibition of DD-10 synthesis in Xenopus embryos at certain preferred sites can interrupt the differentiation cascade taking place locally or can have other, e.g., systemic, effects.

For example, OP-1 treated C2C12 cells provide in vitro model for the above described inhibition of DD-10 synthesis. Briefly, a number of DD-10 antisense oligonucleotides are synthesized by standard procedures as described herein above, based on the sequence depicted in FIG. 6 or SEQ. ID No. 1. Briefly, C2C12 myoblast cells are grown to confluence in DMEM+5% FCS and varying concentrations of each antisense oligonucleotide (1–100 $\mu$M) are then added individually or in various combinations to the C2C12 cells, either at the same time as treatment with 300 ng/ml OP-1, or before or after OP-1 treatment. The effects on cell growth, differentiation and morphology are measured as described herein previously. In addition, the capacity of OP-1 to induce the chondroblast or osteoblast phenotype, e.g., increased alkaline phosphatase mRNA levels or protein synthesis, is determined. DD-10 protein in cell samples is measured as described herein, e.g., by Western blot analysis or sandwich immunoassay using DD-10 specific antibodies. The presence of DD-10 mRNA+ antisense oligonucleotides hybrids is determined by methods known to those skilled in the art such as Northern blot analysis, or RNase H treatment of total RNA. If a ribozyme antisense oligonucleotide is used, cleavage products generated from the cleavage by the ribozyme of DD-10 mRNA can be detected by Northern blot analysis, primer extension analysis or reverse ligation mediated PCR (RL-PCR) using art-recognized techniques.

Varying the time of administration of antisense molecules to the cells can determine how DD-10 participates in the temporal distribution of morphogen activity induced by OP-1, and can further elucidate the role of DD-10 per se in differentiation and/or development of the chondroblastic or osteoblastic phenotype.

In addition, antisense oligonucleotides can be administered to a whole organism, such as a Xenopus embryo and its effects monitored as described herein. Briefly, Xenopus embryos are injected with a suitable amount of an antisense oligonucleotide, e.g., 1–100 mg, of interest at a variety of sites at different stages of differentiation. Organs or organ slices can be analyzed as described in the art and herein above for DD-10 expression or the expression of other differentiation marker proteins in order to determine a requirement for DD-10 expression on morphogenesis/organogenesis.

EXAMPLE 13

Administration of Nucleic Acids Encoding Morphogens, Morphogen Analogs and Morphogen-Responsive Signal Transducers Such As DD-10

Morphogens, morphogen-responsive signal transducers such as DD-10, and/or their protein-based analogs identified using the methods described herein also can be provided to a cell in culture or in vivo, as a nucleic acid. The cells can be primary or transformed cultured cells (e.g., preferably of human, Xenopus, mouse, Drosophila, or Zebra fish origin) or recombinant cells maintained in vitro. Alternatively, the target cells can be located in an animal, for example at a diseased or defective site, and the nucleic acid provided to that site in order to effect or promote its incorporation by local or infiltrated progenitor cells.

In one preferred embodiment, the genetic material is combined with a biocompatible and bioresorbable "matrix" and the resultant "nucleic acid -matrix compound" is provided to the desired site in vivo by standard injection or by standard surgical techniques. Alternatively, the nucleic acid is transfected into appropriate homologous cells, such as explanted host progenitor cells or tissue, and those cells or tissue are combined with an appropriate matrix and similarly introduced to the tissue site. This nucleic acid transfer technique can be used to increase the expression of a gene that is normally expressed, resulting in over expression or it can be used to introduce and effect expression of a gene within a cell or tissue that does not normally express that gene. Methods, compositions, kits, and devices for use in transfecting nucleic acids into progenitor cells, particularly bone cells, for endogenous expression, are described in published PCT application WO95/22611, published Aug. 24, 1995, the disclosure of which is incorporated herein by reference.

The above described nucleic acid can comprise DNA (double or single stranded; linear or circular, e.g., in the form of a plasmid) or RNA (e.g., mRNA). DNA can be derived from genomic sequences, including exons or introns, can comprise only coding portions of a gene, derived from, e.g., cDNA and/or can be entirely biosynthetically produced using rational drug design or random screening methodologies. The DNA molecule, for example, defining a morphogenic gene, can be inserted into any one of the many vectors currently known in the art, in functional association with a suitable promoter. Useful promoters include those normally associated with the gene of interest and/or isolated from any other eukaryotic or bacterial cell that are functional in the progenitor cell. The promoter employed can direct constitutive or inducible gene expression. Currently preferred promoters are CMV, RSV, LTR and the SV40 promoter, and can be in combination with various enhancer and/or activation elements. The nucleic acid segment can be naked DNA or RNA including plasmid DNA, in functional association with recombinant viruses or retroviruses or can be associated with a liposome or a gold particle, the latter of which can be employed in connection with the well-known gene gun technology.

To prepare the nucleic acid segment encoding the morphogenic protein of interest, one can follow the teachings disclosed herein and also the teachings of any of the patents or scientific documents specifically referenced herein. One can thus obtain DNA segments using molecular biological techniques such as PCR, Differential Display, or screening a cDNA or genomic library, using primers or probes with sequences based on the nucleotide sequence of interest. The practice of such techniques is a routine matter for those of ordinary skill in the art, as taught in various scientific articles, such as Sambrook et al (1989), incorporated herein by reference as stated above.

It is understood that one or more than one gene sequence of interest can be used in the transfection methods provided herein. Thus administration of one, two, three, or more gene sequences is contemplated. The maximum number of gene sequences that can be applied is limited only by practical considerations, such as the possibility of eliciting a significant adverse cytotoxic effect. Certain nucleic acid combinations can be chosen or designed to achieve synergistic effects on, for example, cell stimulation, differentiation and tissue growth. If desired, the nucleic acid segment could be administered in combination with further agents, such as, e.g., proteins or polypeptides or various pharmaceutically active agents. Indeed, many synergistic effects have been described in the scientific literature, so that one of ordinary skill in the art would readily be able to identify likely synergistic gene combinations, or even gene-protein combinations.

The choice of matrix material differs according to the particular circumstances and the tissue site that is to be tested or treated. Matrices such as those described in U.S. Pat. No. 5,270,300 (incorporated herein by reference) can be employed. Physical and chemical characteristics, such as, e.g., biocompatibility, bioresorbability, biodegradability, strength, rigidity, interface properties, and even cosmetic appearance, can be considered in choosing a matrix, as is well known to the skilled artisan. Appropriate matrices can deliver the gene composition following disassociation at the cell surface or in the immediate cellular environment. In certain circumstances, the nucleic acid impregnated matrix can be incorporated into a cell by active or passive membrane transport and provide subsequent intracellular release of the genetic material at a variable rate, depending upon the types of matrix used. The matrix can then be extruded from the cell, catabolized by the cell, or even stored within the cell. Properties of the matrix and nucleic acid composition, known to those skilled in the art, can be assessed in optimizing the matrix nucleic acid formation. Further, the matrix material can act as an in situ scaffolding on which progenitor cells can grow or through which they can migrate.

In certain embodiments, non-biodegradable matrices can be employed, such as sintered hydroxylapatite, aluminates, other bioceramic materials and metal materials, particularly titanium. For example, when the morphogenic nucleic acid matrix is used in connection with orthopedic implants, it is contemplated that the metal surface or surfaces of the implant, such as a titanium surface, will be coated with a material that has an affinity for nucleic acids, most preferably, with hydroxyl apatite, and then the coated-metal will be further coated with the gene or nucleic acid that one wishes to transfer. The available chemical groups of the absorptive material, such as hydroxyl apatite, can be readily manipulated to control its affinity for nucleic acids, as is known to those of skill in the art. A suitable ceramic delivery system is that described in U.S. Pat. No. 4,596,574, incorporated hereby by reference. Polymeric matrices, including acrylic ester polymers, lactic acid polymers, and polylactic polyglycolic acid (PLGA) block copolymers, have also been disclosed (U.S. Pat. Nos. 4,526,909, 4,563,489, Simons et al., 1992, and Langer and Folkman, 1976, respectively, each incorporated herein by reference). PGLA block copolymers have the advantageous properties of sustained release of pharmaceutical agents, a capacity for reversible thermal gelation, and an ability to combine with other agents that allow for radiographic visualization. "Reversible thermal gelation" is the ability of the nucleic acid matrix composition to be a liquid at 4° C. and to form a gelatinous matrix upon equilibration toward body temperature.

A biodegradable matrix is currently preferred. A biodegradable matrix is generally defined as one that is capable of being resorbed into the body. Potential biodegradable matrices for use in connection with the compositions, devices and methods described herein include, for example, biodegradable and chemically defined calcium sulfate, tricalciumphosphate, hydroxylapatite, PLGA block copolymers, polyanhydrides, matrices of purified proteins, and semi-purified extracellular matrix compositions.

One currently preferred group of matrices are collagenous matrices, including those obtained from tendon or dermal collagen, e.g., type I collagen, which is generally prepared from dermis; those obtained from cartilage, such as type II collagen; and various other types of collagen. Type II collagen can be a preferred matrix for stimulating bone growth, for example, because of its ability to stimulate bone progenitor cells, absent even of the presence of any osteotopic gene. Collagen matrices can be obtained from a variety of sources or be prepared as described in U.S. Pat. Nos. 4,394,370 and 4,975,527, each incorporated herein by reference. The various collagenous materials can also be in the form of mineralized collagen, such as UltraFiber™, obtainable from Norian Corp. (Mountain View, Calif.) U.S. Pat. No. 5,231,169, incorporated herein by reference.

Once a suitable matrix-nucleic acid composition has been prepared or obtained, the composition is placed in contact with the desired cultured cell or the site in the body of the animal in which one wishes to promote morphogenesis and tissue growth. This can be achieved by physically positioning the matrix-nucleic acid composition in contact with the desired body site, or by injecting a syringeable form of the matrix-nucleic acid composition into the desired body site.

Alternatively, genes of interest and DNA segments thereof can be in the form of a DNA insert which is located within the genome of a recombinant non-lytic virus, such as, for example, a recombinant adenovirus, adeno-associated virus (AAV) or retrovirus. Recombinant viral particles are prepared by standard methods, and placed in contact with the progenitor cells or tissues whereby the virus infects the cells and transfers the genetic material into the host's genome. One can also impregnate a suitable matrix with recombinant virus and then contact the progenitor cells or tissues with the resultant virus impregnated matrix. It is expected that the recombinant virus will become incorporated into the host genome and acquire and express the DNA of interest.

To prepare one of the exemplary compositions contemplated herein, an appropriate matrix material, such as e.g. collagen type II, is soaked with 0.5–1.0 mg/ purified recombinant adenovirus in an aqueous solution such as water or an acceptable buffer prior to placement into a tissue site. One such tissue site exploits the rat osteotomy model provided in WO95/22611 as earlier cited and incorporated by reference above. Briefly, Adult Sprague Dawley rats are anesthetized using a 3% halothane, 97% oxygen mixture (700 ml/min. flow rate) and a 5 mm or 2 mm segmental defect is created in the central diaphysis through an incision using an Hall micro 100 oscillating saw (#5053-60 Hall surgical blades) under constant irrigation. The osteotomy site is irrigated with sterile saline and a fibrous collagen implant material, previously soaked in a solution of plasmid DNA (such as, for example, recombinant adenoviral DNA comprising a morphogen or morphogen analog identified by the methods disclosed herein) or other DNA construct, is placed in situ. The wound is then closed in layers. No significant adverse effects are reportedly observed with this procedure. A wide variety of art known procedures, including those described herein, can be used to detect the presence of mRNA and protein synthesized by cells having taken up and expressing the implanted DNA. Furthermore, it is expected that tissue-specific morphogenesis will be observed at the implantation site using techniques known to those skilled in the art, such as those described above.

Additionally, expression of the transgene at the site of bone regeneration can be assessed by in situ hybridization. This method is also useful in detecting the expression of other molecules at the site (e.g. mRNAs encoding other morphogen-responsive genes in the cascade). This method can be used in place of, or in addition to, Northern blot analysis or RT-PCR. Alternatively the site of tissue regeneration can be analyzed, for example, using immunofluorescent analysis of tissue slices, using specific antibodies, as described previously herein.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. An isolated nucleic acid comprising nucleotides 905-1264 of SEQ ID NO: 1.

2. An isolated nucleic acid comprising nucleotides 121-780, 600-900, or 1-904 of SEQ ID NO: 1.

3. An isolated nucleic acid comprising nucleotides 1-1264 or 1-3611 of SEQ ID NO: 1.

4. An isolated nucleic acid selected from the group consisting of aliclic, biosynthetic, species, and recombinant variants of a nucleic acid according to claim 1, 2, or 3.

5. A fragment of a nucleic acid according to claim 1, said fragment encoding a polypeptide having DD-10 biological activity.

6. A nucleic acid which hybridizes to the DNA shown in SEQ ID NO: 1 or the complementary strand thereof, wherein said nucleic acid, or the complementary strand thereof, encodes a DD-10 polypeptide.

7. A vector comprising nucleotides 905-1264, 121-780, 600-900, 1-904, 1-1264, 1-3611, or 1264-3611 of SEQ ID NO: 1, or a biologically-active fragment thereof.

8. A cell transfected with a nucleic acid comprising nucleotides 905-1264, 121-780, 600-900, 1-904, 1-1264, 1-3611, or 1264-3611 of SEQ ID NO: 1, or a biologically-active fragment thereof.

9. A cell transformed with a vector of claim 7.

10. A method for identify a compound that induces a morphogen-mediated biological effect, the method comprising the steps of.

a) determining a basal level of expression of a DD-10 genetic sequence in a sample;

b) exposing said sample to a candidate compound;

c) determining a test level of expression of a DD-10 genetic sequence; and d) comparing said DD-10 test level obtained in step c) with said basal level;

wherein a compound that induces a morphogen-mediated biological effect is identified as one that induces a DD-10 test level above said basal level.

11. The method according to claim 10 wherein said DD-10 genetic sequence is complementary to SEQ ID NO: 1, or the complementary strand thereof.

12. The method according to claim 11 wherein said DD-10 genetic sequence comprises a nucleic acid selected from the group consisting of nucleotides 1-904 of SEQ ID NO: 1, nucleotides 600-900 of SEQ ID NO: 1, and nucleotides 121-780 of SEQ ID NO: 1.

13. The method according to claim 11 wherein said DD-10 genetic sequence is in operative association with a reporter gene.

14. The method according to claim 10 wherein the level of expression of said DD-10 genetic sequence is determined by detecting an expression product comprising an RNA or a polypeptide.

15. The method according to claim 14 wherein said RNA is transcribed from the nucleic acid shown in SEQ ID NO: 1.

16. The method according to claim 14 wherein said polypeptide is the DD-10 polypeptide shown in SEQ ID NO: 2, or a fragment thereof.

17. The method according to claim 10 wherein said test level of expression is determined 1 to 30 hours following said exposing step.

18. The method according to claim 10 wherein said test level of expression is determined 2 to 10 hours following said exposing step.

19. The method according to claim 10 wherein said morphogen-mediated biological effect is an OP-1-mediated biological effect.

20. The method according to claim 10 wherein said sample comprises cells having a receptor for OP-1.

21. A method for inducing a morphogen-mediated biological response, said method comprising the step of contacting a precursor cell with a DD-10 nucleic acid under conditions sufficient to obtain expression of said nucleic acid, wherein expression of said nucleic acid induces a morphogen-mediated biological response.

22. The method according to claim 21 wherein said precursor cell is a myoblast cell or a cell of the myoblast/chondroblast/osteoblast lineage.

23. The method according to claim 21 wherein said precursor cell is an osteoblast cell.

24. The method according to claim 21 wherein said DD-10 nucleic acid hybridizes to a nucleic acid shown in SEQ ID NO: 1 or the complementary stand thereof.

25. A method for detecting a morphogen-mediated biological effect comprising the step of detecting an expression product of a nucleic acid of SEQ ID NO: 1, wherein detection of said expression product is indicative of a morphogen-mediated biological effect.

26. The method according to claim 25 wherein said biological effect is chondroblast or osteoblast differentiation.

27. The method according to claim 25 wherein said expression product is an RNA or a polypeptide.

28. An oligonucleotide complementary to at least 8 contiguous nucleotides of SEQ ID NO: 1, or the complementary strand thereof.

29. An oligonucleotide of claim 28 consisting of 10–30 nucleotides.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 3611 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 905..1264

(xi) SEQUENCE DESCRIPTION: SEQ ID NO:1:

```
GAAGTGTGCT ATTCTACCAG CTATTTGGTA TCTCTAGGGC AACAAACTTG ACAATCAAGA    60

TCAGCTACCA CATGCCTCTC TCCTCGATAA AGAGCAAGCT GCGAAGGGCG ATTACAGCTG   120

GACACAGGTG AGTGAGCCAG AAGGAACTGA CCAGCCTTAG GAAGGAACCG TCACAGCTAG   180

GCCATGCTCC AGATATTAAT TTCTGAGTCA CTGGCCAGGA GCGAGATCCC AGTGTAAGAG   240

TCCCCTGTGA TGTAACGTCT GGAAGAATTC ACAGAGAAA GAAGTCAGAA ACTTCTACAC    300

AGCTGACAGA TCAAGATCAC CAGGGCTGGG AAGTTTTCTC AGGAGTAAAG TGTGAGGAGC   360

GGAGTTTAAA TCCCAGCAGC CGTGTAAAAG CTGCTGCAGG AGCATGTCTG CAATCTCAGG   420

CCTGGGGGAA GTGAGCAAAG ACAGCAGCTG CTGAGAACTT ACTGGGCAGC CGTGGAGACA   480

AAGTGCCAAG CTCCAGATTC CGTGGGAGCC CCAGGAAATA AGGTGAAAGA ACAAGATGTA   540

GAAAGAACTC TCAGCTTCCT CAGCATCCTG TCTGCCTGCC TTCAAGCTTT CGTGCTTCCC   600

ACCATGATGA CAACGGACTG AACCTCAGAA TCTACAAGTC AGCCCCAATT AAATGTTGTT   660

TTAGTCATGG TGTCTTTTCA CAGCAATGAA AATTCTAAGA TAGAAGTTAC TAACAAGGAC   720

TAGGGTATTG CTGTGATGGG CCTGACCATG CTTTTGTGGA TTTTGTAACT TTGGATTTGG   780

AAAGCAGTGG AATGCTTTAA GTGGGACTTA ATGGACAGC CTAGTAGGAA TAGGGAGGAC    840

ATTGGTGCTA AGGGTGAACT CTGCGGGTCT GGCTCAAGAG ATTTCAGAGG AGAATAACTT   900

GAGT ATG TGG CCT GGA GAC TGC TTT TGT GAT ACT TTG GTG AGG AAT GTA    949
     Met Trp Pro Gly Asp Cys Phe Cys Asp Thr Leu Val Arg Asn Val
      1               5                  10                  15

GGT ACT TTT TGC CCT CGT TTG AAG TGT CTG CCT GAG GCT CAA GTG AAG     997
Gly Thr Phe Cys Pro Arg Leu Lys Cys Leu Pro Glu Ala Gln Val Lys
                 20                  25                  30

ACA TTC AAA TTA ATT GCA ATG ACA GAA GTC TCA GAA AAG GGG CAA GTC    1045
Thr Phe Lys Leu Ile Ala Met Thr Glu Val Ser Glu Lys Gly Gln Val
             35                  40                  45

CAA TCT TCA TCA TCA GGA TAT CTT CAA TCA GCA ACC AGC AAA AAA CAG    1093
Gln Ser Ser Ser Ser Gly Tyr Leu Gln Ser Ala Thr Ser Lys Lys Gln
         50                  55                  60

CAA AAC AGC AAA TGC AAC AGC AGG AAC CAG CAA CAG CAG GAA GAG CAG    1141
Gln Asn Ser Lys Cys Asn Ser Arg Asn Gln Gln Gln Gln Glu Glu Gln
     65                  70                  75

CAG CCA CTA CCT CCT CTG GTG TTT ATA TAC TGC TCT GGT ATT TAT ATT    1189
Gln Pro Leu Pro Pro Leu Val Phe Ile Tyr Cys Ser Gly Ile Tyr Ile
 80                  85                  90                  95

CTC TCT CAA GAA TTC CTA GAA ATC TAC TGT CTT CAG CTG GCA AAT CAC    1237
Leu Ser Gln Glu Phe Leu Glu Ile Tyr Cys Leu Gln Leu Ala Asn His
```

-continued

```
               100              105              110
ATC CCT GCC AGA GCA CGA GAC AAA TCA TAGTCAGCTG CTGTGGACAA              1284
Ile Pro Ala Arg Ala Arg Asp Lys Ser
             115              120

TCTGAAGCAG ACCCACATCC CACCCCTGGA ATTAAAACAA AAACACATTC ATAGAACATA      1344

ACTAGGGGGA AAAAAAACCA ATACAGTGAG CTTTGGGATG GCCAGCTTTC TTACACGGAG      1404

GCTCAGAGCT CCACAGTAAG AGAGGGTGGT GGGAGTGGTG ACAGGTAGAA AGACTGTCAT      1464

CTTTCATGAC TGCCTGCATA AGAAGCTAAG CCCCAGGGAT AGAGGCTCAG CCTCTTTATG      1524

AAAGAATAGC ATGGCTCTAA AGAACATGT TTAGAGGGAA AGACTATTAG AGCCATATTT       1584

TGGAAAATAT AATGAGACAC AATATTTTTT TGTGGATACA GTTTTATAAT AAGGGTGGTA     1644

GCAGGAAATG TCTCCTGACC ACCACCTGCT ATCCTGATGA GGGAACCAGC TGCTATTTGG     1704

ATGCCTGTGG TAAATACCAC CCACTTTGAT GCCATCACTC TGATAGCCCA GACTCACTTA     1764

CAACCCCTTC ACTGGGGAAA GAGGGATTTT TGGTATTACA GCTGCCATCA TTGCAGCCAT     1824

TATTGCAGGT ATTACAGGGG CAACAACAGC TACTGTTGCC CAGACCGCCA CTATGAGAGG     1884

CTGTCAACGC TGTAGTCTCT AAGTCAGCTG AGGTGCTACA GGCATAGGAG CTACTAAATC     1944

AACATCTTTA TGAGGCCATC ACATTTTAC AACAACAGAT TGACTGGCAG AAGAGCTGGC      2004

TCTTGTTAGG GACATGTGTC TATGGGCCTG TGACCCAGGT TTCACTCAAT CTACCTAACC    2064

CTTTACCAAG TACATAATGC CACTGAAGCC CAACAACAGT TGGCTCAATA GCTTAAAGAT    2124

ACCTAGTCAG ACAAATTCCT ATTCCTGAAG GCAAGAAAAC CACTCACTTG CCCAATTGGT    2184

GGTAGATATA ACCACGTCCA TAACCAACTT TGGAAGCGGG AACCAGGGCT CCTATGACAG    2244

AAAAGAAGCA GGCTTCTCTC TGCAATTCAT AAACACCGAC AGGAATATGT TGCTTTTCCT    2304

AAGCCCTTCG CTGTCTTTCC AAGAAGAATT TTTTTGTCCT TAACCAAATG TGAAATGCAC    2364

ATTTTGAGCA CAAAGAATCA AAGCTCCAAC AGCAAACTGA CATGACATCC TTTACAGGAA    2424

GTAAAATATT TAAAGACAGA TTCAGAGTCT TCTATTCCCC TCCCCCCAGG AAGAAACCCT    2484

TTAATATTCC GATTAACCTT GATGTGAATC ACAGCGCTCC TTCTTCCCTG TAGGCAGATA    2544

ATCATGACTC ACCACAGACC CCTGACTGTG GGCTTCATGT AATTCTGGCA GCAAAGGCCT    2604

TCCTTTGCTG TGTGAGGCCA TTGGCTGTGA ATCTTTACA AAGTCCAGGG ATGGACTAGG     2664

AGTAACCCTG GAGCAAGCTT TGCACTGTGT ATCAAAACAA GACTCCACAT TGGGGCATCC    2724

ACACTGAGGC CACCTTGTGA ACTAGGCCTC ACCTTGGATA AGAAAGAAAT TGCATTATTT    2784

TTACTTTCAA ATGTGTTAAA GAATAAATTT TACTTAAATA TATTCTATAT TCAATCAGAT    2844

ATGCCCACTG CTGGAGACTG AGTATTTGTG TTTTACACCA AAATTTCTTT TGAAACCTAA    2904

GCCCTAAGGA GATAGCATCA GGAAGTGGGG TTGTTGGAAG TGATTAGGTC ATAAGGCAGA    2964

GTCTTCATAA ATAGTATTCT TACTTTGATA AAAAGAGATC CAGAGAATTC AATGGCCCCC    3024

TACATCAGTG AGGATACAGA AAAAAGTTGT CAAGGGAGTT TCCCTGGAC CCTGCCACCC    3084

TGACATCGAG TTGGGCTCCA GACTCCAGAA CTCTAAGAAC TAAATTTCCA CTGTTGATAC    3144

GGTACCTGGC CCAAGGTATT TCAATGTAGA ATTTAAAATG GATAAAGACA GCCACTTCTA    3204

TGCACAGTTC GAGTGTAAGC ATGCTCTACA CTACAGACAG GTTAACCACT CTCCATACAT    3264

TAATGTGGTC TCTACACTAC TGATACATAG TAACCACTCT CCATAAACTT AATATGCTCT    3324

CTACACTACT TATACATTGT AACTACTCTC CCGGTACAGT TAGTCTACTC TCCACTCTAA    3384

AAAGCAGGAT AGAACATGAG GATGGGGAA GGTAGCTCTG TCAATAGAAA ATGTTTGCCT    3444

TTCGAACCTG GAGTTTGATC CCAGAGCCAA CATTGAAAAG GCAGTGGTGG GCAGTGCATA    3504
```

```
AAAATCCCAG CACCACAGAG GCAGAGACAG GCTCTGATTG ACTGACCAGC CTAGTTTAGT      3564

CTATGAACTT CAAGCCATAA TTTTGTCTGA AAAAGAAAGA AAGAAAG                   3611
```

(2) INFORMATION FOR SEQ ID NO:2:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:2:

```
Met Trp Pro Gly Asp Cys Phe Cys Asp Thr Leu Val Arg Asn Val Gly
 1               5                  10                  15

Thr Phe Cys Pro Arg Leu Lys Cys Leu Pro Glu Ala Gln Val Lys Thr
                20                  25                  30

Phe Lys Leu Ile Ala Met Thr Glu Val Ser Glu Lys Gly Gln Val Gln
            35                  40                  45

Ser Ser Ser Ser Gly Tyr Leu Gln Ser Ala Thr Ser Lys Lys Gln Gln
        50                  55                  60

Asn Ser Lys Cys Asn Ser Arg Asn Gln Gln Gln Glu Glu Gln Gln
65                  70                  75                  80

Pro Leu Pro Pro Leu Val Phe Ile Tyr Cys Ser Gly Ile Tyr Ile Leu
                85                  90                  95

Ser Gln Glu Phe Leu Glu Ile Tyr Cys Leu Gln Leu Ala Asn His Ile
                100                 105                 110

Pro Ala Arg Ala Arg Asp Lys Ser
            115                 120
```

(2) INFORMATION FOR SEQ ID NO:3:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Leu Leu Phe Glu Arg Met Trp Ile Phe Gly Leu Trp Ile Trp Lys
 1               5                  10                  15

Ala Val Glu Tyr Phe Lys Trp Gly Leu Met Gly His Pro Ser Arg Asn
                20                  25                  30

Met Glu Asp Phe Val Ala Gly Ser Asn Leu Asn Cys Val Asp Leu Ala
            35                  40                  45

Gln Glu Ile Ser Lys Glu Lys Asn Phe Arg Met Trp His Lys Asp Cys
        50                  55                  60

Phe Cys Gly Ile Leu Val Lys Asn Val Ala Thr Phe Cys Pro Cys Leu
65                  70                  75                  80

Lys Ser Gln Pro Glu Ala Lys Val Lys Gly Ile Arg Leu Ile Ala Leu
                85                  90                  95

Thr Lys Asp Ile Ser Lys Lys Leu Ser Arg Asp Phe Val Leu
                100                 105                 110
```